US008067398B2

(12) United States Patent
Katzhendler et al.

(10) Patent No.: US 8,067,398 B2
(45) Date of Patent: Nov. 29, 2011

(54) BIODEGRADABLE POLYMERS HAVING A PRE-DETERMINED CHIRALITY

(75) Inventors: Yehoshua Katzhendler, Jerusalem (IL); Abraham Jackob Domb, Efrat (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 664 days.

(21) Appl. No.: 11/921,214

(22) PCT Filed: Jun. 4, 2006

(86) PCT No.: PCT/IL2006/000643
§ 371 (c)(1),
(2), (4) Date: Nov. 29, 2007

(87) PCT Pub. No.: WO2006/129320
PCT Pub. Date: Dec. 7, 2006

(65) Prior Publication Data
US 2009/0318339 A1 Dec. 24, 2009

Related U.S. Application Data

(60) Provisional application No. 60/686,009, filed on Jun. 1, 2005.

(51) Int. Cl.
*A01N 37/36* (2006.01)
(52) U.S. Cl. ........ 514/159; 528/271; 528/272; 528/288; 528/291; 528/363; 524/17; 524/599; 530/300; 424/78.08; 424/94.1; 424/408; 424/409; 424/426; 349/133
(58) Field of Classification Search ............... 424/78.08, 424/94.1, 408, 409, 426, 428; 514/2, 5, 159, 514/579; 530/300, 317; 528/206, 207, 208, 528/209, 248, 259, 271, 272, 288, 290, 291, 528/292, 293, 294, 295, 355, 356, 361, 363; 349/76, 133, 136, 172, 179; 524/17, 21, 524/599
See application file for complete search history.

(56) References Cited

U.S. PATENT DOCUMENTS

| | | | |
|---|---|---|---|
| 4,326,031 A | 4/1982 | Wandrey et al. | |
| 4,999,417 A * | 3/1991 | Domb ............................ | 528/271 |
| 5,098,841 A | 3/1992 | Ghisalba et al. | |
| 5,686,275 A | 11/1997 | Casey et al. | |
| 5,844,068 A * | 12/1998 | Otera et al. ................... | 528/361 |
| 7,622,544 B2 * | 11/2009 | Braun ............................ | 528/272 |

FOREIGN PATENT DOCUMENTS

| | | |
|---|---|---|
| WO | WO 99/36100 | 7/1999 |
| WO | WO 02/16552 | 2/2002 |
| WO | WO 02/33110 | 4/2002 |
| WO | WO 2007/050732 | 6/2004 |
| WO | WO 2006/129320 | 12/2006 |

OTHER PUBLICATIONS

Bou et al. "Optically Active Polyamides Derived From L-Tartaric Acid", Macromolecules, 26(21): 5664-5670, 1993. Scheme 1, Experimental Part.
Hrkach et al. "Synthesis of Poly(L-Lactic Acid-Co-L-Lysine) Graft Copolymers", Macromolecules, 28(13): 4736-4739, 1995. Experimental Partfig.1 .
Kuisle et al. "Solid Phase Synthesis of Depsides and Depsipeptides", Tetrahedron Letters, 40(6): 1203-1206, 1999. Scheme 1, 2.
Communication Relating to the Results of the Partial International Search Dated Oct. 10, 2006 From the International Searching Authority Re.: Application No. PCT/IL2006/000643.
International Preliminary Report on Patentability Dated Dec. 21, 2007 From the International Bureau of WIPO Re.: Application No. PCT/IL2006/000643.
Communication Pursuant to Article 94(3) EPC Dated Jul. 29, 2009 From the European Patent Office Re.: Application No. 06756190.2.
Communication Pursuant to Article 94(3) EPC Dated Apr. 16, 2008 From the European Patent Office Re.: Application No. 06756190.2.
International Search Report Dated Dec. 4, 2006 From the International Searching Authority Re.: Application No. PCT/IL2006/000643.
Partial International Search Report Dated Oct. 10, 2006 From the International Searching Authority Re.: Application No. PCT/IL2006/000643.
Written Opinion Dated Dec. 4, 2006 From the International Searching Authority Re.: Application No. PCT/1L2006/000643.
Bishara et al. "PLA Stereocomplexes for Controlled Release of Somatostatin Analogue", Journal of Controlled Release, 107: 474-483, 2005.
Bonthrone et al. "The Biological and Physical Chemistry of Polyhydroxyalkanoates as Seen by NMR Spectroscopy", FEMS Microbiology Reviews, 103: 269-278, 1992.
Brandl et al. "Plastics From Bacteria and for Bacteria: Poly(?-Hydroxy-Alkanoates) as Natural, Biocompatible, and Biodegradable Polyesters", Advances in Biochemical Engineering/Biotechnology, 41: 787-793, 1990.
Corey et al. "A New System for Catalytic Enantioselective Reduction of Achiral Ketones to Chiral Alcohols. Synthesis of Chiral ?-Hydroxy Acids", Tetrahedron Letters, 31(5): 611-614, 1990. Mergaert et al. "Biodegradation of Polyhydroxyalkanoates", FEMS Microbiology Reviews, 103: 317-322, 1992.
Reddy et al. "Chirality and Its Implications in Transdermal Drug Development", Critical Reviews in Therapeutic Drug Carrier Systems, 17(4): 285-325, 2000.

(Continued)

Primary Examiner — James J Seidleck
Assistant Examiner — Frances Tischler

(57) ABSTRACT

Optically active polymers that are composed of monomer residues derived from chiral pre-polymerized monomers, which maintain the chirality of the pre-polymerized monomers upon polymerization are disclosed. These polymers can be composed of monomer residues that are derived from readily available chiral monomers and can be designed to have pre-determined characteristics such as chirality, biodegradability and functionality. Uses of these polymers as therapeutically active agents, and/or as carriers of therapeutically active agents, for delivering the active agents to a targeted bodily site and/or for a sustained release of the active agent, are further disclosed. Also disclosed are processes of preparing the polymers, compositions and medical devices containing the polymers, and conjugates of these polymers and various agents.

35 Claims, 1 Drawing Sheet

OTHER PUBLICATIONS

Seebach et al. "Detection, Synthesis, Structure, and Function of Oligo(3- Hydroxyalkanoates): Contributions by Synthetic Organic Chemists", International Journal of Biological Macromolecules, 25: 217-236, 1999.

Stager et al. "Biopolymer Stereocomplexes", Advanced Drug Delivery Reviews, 55: 549-583, 2003.

Stager et al. "Hetero-Stereocomplexes of D-Poly(Lactic Acid) and the LHRH Analogue Leuprolide. Application in Controlled Release", European Journal of Pharmaceutics and Biopharmaceutics, 58: 461-469, 2004.

Slager et al. "Heterostereocomplexes Prepared From D-PLA and L-PLA and Leuprolide. II Release of Leuprolide", Biomacromolecules, 4: 1316-1320, 2003.

Slager et al. "Heterostereocomplexes Prepared From D-Poly(Lactide) and Leuprolide. I. Characterization", Biomacromolecules, 4: 1308-1315, 2003.

Slager et al. "Peptides Form Stereoselective Complexes With Chiral Polymers", Macromolecules, 36: 2999-3000, 2003.

Slager et al. "Stereocomplexes Based on Poly(Lactic acid) and Insulin: Formulation and Release Studies", Biomaterials, 23: 4389-4396, 2002.

Vert et al. "New Insights on the Degradation of Bioresorbable Polymeric Devices Based on Lactic and Glycolic Acids", Clinical Materials, 10: 3-8, 1992.

References Considered Except W I-Ere Lined Ti Irougi I.

* cited by examiner

Category A hAA

1A

2A

3A

4A $R, R_1, R_2, R_3, R_4$ = Side chain of Amino Acids

Category B

1B

2B $Y = (CH_2)m, (CH_2CH_2O)_k$;
$R; R_1$ = Amino acids side chains

Category C

1C

R = Amino acids side chain; $CH_2O-P$
(P = protecting group)

2C $Y = [CH(R)-CH(R')]m$, where R and R' are hydrogens
Z = O, NH

Category D

1D

R = Amino acids side chains
(P = protecting group)

BIODEGRADABLE POLYMERS HAVING A PRE-DETERMINED CHIRALITY

RELATED APPLICATIONS

This Application is a National Phase of PCT Patent Application No. PCT/IL2006/000643 having International Filing Date of Jun. 4, 2006, which claims the benefit of U.S. Provisional Patent Application No. 60/686,009 filed on Jun. 1, 2005. The contents of the above Applications are all incorporated herein by reference.

FIELD AND BACKGROUND OF THE INVENTION

The present invention relates to novel polymers and, more particularly, to biodegradable polymers which have a pre-determined chirality, to processes of preparing such biodegradable polymers, to heterostereoselective complexes, conjugates and compositions containing same and to uses thereof.

Biodegradable polymers are polymeric materials that undergo chemical, metabolic (by biological processes such as hydrolysis or enzymatic digestion) and/or mechanical breakdown, in a biological environment (e.g., within a body of a living organism, in the presence of microorganisms, and/or in a biological medium). The biodegradability of such polymeric materials renders them highly suitable for constructing environmental-friendly products, and for use in a myriad of medical applications.

Biodegradable polymeric materials have therefore been used for many years in diverse fields, including, for example, agriculture, fishing materials, sanitation, and articles for everyday life (e.g., masks, wet tissues (wipes), underwear, towels, handkerchiefs, kitchen towels and diapers). Medical applications that utilize biodegradable polymers include, for example, orthopedic surgery, including fixation of fractures, bone replacement, cartilage repair, meniscal repair, and fixation of ligament; absorbable devices such as screws, pins, plugs, and plates for orthopedic, oral, and craniofacial surgery, as well as absorbable sutures; scaffolds for tissue engineering; and as drug carriers. The use of biodegradable drug carriers is the most effective route for delivering a drug, since it enables a sustained systemic release of the drug while circumventing the undesired residual impact of the carrier.

Since non-toxicity is an inherent prerequisite for biodegradable polymers that are designed for medical applications, the starting materials, the final product and the optional breakdown products of such biodegradable polymers should be non-toxic and benign. Breakdown products should preferably be also small, water-soluble molecules.

The total degradation time of biodegradable polymers can vary from several days to several years, depending mainly on the chemical structure of the polymer chains, and physical properties such density, surface area and size of the polymer.

When used in medical applications, the biodegradable polymer of choice for the intended use is selected according to its properties. Thus, for example, semi-crystalline polymers (e.g., poly(L-lactic acid)) are typically used in medical devices that require good mechanical properties such as sutures, devices for orthopedic and cardiovascular surgery, and stents. Amorphous polymers, on the other hand (e.g., poly(DL-lactic-co glycolic acid)), are attractive in drug delivery applications, where it is important to have homogenous dispersion of the active species within the polymeric matrix.

The degradation rate of biodegradable polymers is determined by various factors such as the initial molecular weight, the exposed surface area, and the polymer's degree of crystallinity, the quantitative ratio of the monomers, in the case of co-polymers, the chirality of the polymer (racemic mixture versus pure enantiomeric or diastereomeric form), the presence of additives or impurities, the mechanism of degradation (e.g., enzymatic cleavage versus hydrolysis), the implantation site (e.g., subcutaneous tissue versus bone), the actual stress the polymer is subjected to, and even the age of the host subject.

Biodegradability is typically accomplished by synthesizing or using polymers that have hydrolytically unstable linkages in the backbone. Chemical hydrolysis of the hydrolytically unstable backbone is the prevailing mechanism for the polymer's degradation. Biodegradable polymers can be either natural or synthetic. Synthetic polymers commonly used in medical applications include, for example, polyethylene glycol, polyvinyl alcohol, and poly(hydroxypropyl-metacrylamide). In addition, natural polymers are also used in medical applications. For instance, dextran, hydroxyethyl-starch, albumin and partially hydrolyzed proteins find use in various applications ranging from plasma substitute, to radiopharmaceutical to parenteral nutrition.

In general, synthetic polymers may offer greater advantages than natural materials in that they can be tailored to give a wider range of properties and more predictable lot-to-lot uniformity than can materials from natural sources. Synthetic polymers also represent a more reliable source of raw materials, one free from concerns of infection or immunogenicity.

Methods of preparing polymeric materials are well known in the art. However, synthetic methods that successfully lead to the preparation of polymeric materials that exhibit adequate biodegradability, biocompatibility, hydrophilicity and minimal toxicity for medical use are scarce. The restricted number and variety of biopolymers currently available attest to this.

The presently used biodegradable polymers for medical applications can be classified by their chemical structure as follows:

Polysaccharides, such as starch, cellulose, chitine, chitosan, and alginic acid;

Polypeptides of natural origin, such as gelatin;

Polymers having carbon backbones, such as polyvinyl alcohol and polyvinyl acetate; and Polymers having a hydrolyzable backbone, such as polyesters, polycaprolactones, polyamides, polyurethanes, polyanhydrides and poly(amide-enamines).

Some commonly used biodegradable polymers are co-polymers, which are composed of various combinations and variations of hydrolysable polymers.

One of the most appealing groups of biodegradable polymers is the family of polyesters, which are characterized by a —O—R—C(=O)— repeating unit, in which the ester bonds are easily hydrolyzed to hydroxy carboxylic acid monomers when placed in aqueous medium.

Polyesters can be synthesized by polycondensation of diols and dicarboxylic acids, by self-polycondensation of hydroxy carboxylic acids, or by ring opening polymerization (ROP) of cyclic esters (lactones), in bulk or in solution.

Polycondensation can be applicable for a variety of combination of monomers, but generally requires high temperature and long reaction time to obtain high molecular weight polymers. In addition, the chain length of the obtained polymers cannot be controlled. If higher molecular weight polymers are needed, the initially obtained polymers can be further cross-linked, by using, for example, diisocianates, bis (amino-ethers), phosgene, phosphate and anhydrides. The most useful monomers for polycondensation are lactic, glycolic, hydroxybutyric and hydroxycaproic acids, polymers of which are known for their long history of safety.

Ring-opening polymerization can be performed only with a limited number of monomers, but can be carried out under milder reaction conditions and produces high molecular weight polymers in short time, as compared to polycondensation polymerization. Furthermore, recent progress in catalysts and initiators for living polymerization has enabled obtaining polyesters of controlled chain length.

A particularly advantageous subfamily of polyesters includes the poly hydroxyalkanoates (PHAs). PHAs are naturally produced by numerous microorganisms as energy reserve materials in the presence of excess carbon source when an essential nutrient, such as nitrogen or phosphorus, is available only in limiting concentrations. PHAs also form a part of depsipeptides, bio-oligomers ubiquitous in nature, which are composed of hydroxy and amino acids linked by amide and ester bonds. Depsipeptides have recently shown to exhibit high therapeutic potential as anticancer, anti-viral, antibacterial, antifungal, anti-clotting, anti-antherogenic and anti-inflammatory agents [Villar-Garea and Esteller, Int. J. Cancer:2004:112:171-178; Sparidans et al., Biomed. Chromatogr. 2004:18: 16-20; and Mayer and Gustafson, *Int. J. Cancer:* 2003:105, 291-299]. Depsipeptides are regarded, together with amino acids, as components in the natural chiral pool.

PHAs completely degrade into water and carbon dioxide under aerobic conditions, and into methane under anaerobic conditions by a variety of soil, sea, lake and sewage microorganisms. PHAs exhibit a wide variety of mechanical properties, from hard crystalline to elastic, depending on the nature of the monomer units. For example, MCL-PHAs (medium chain length: 6-10) are semi-crystalline elastomers with low melting point, low tensile strength and high elongation to break, and can be used as biodegradable rubber after cross linking. Some PHAs possess properties of thermoplastics.

Poly(3-hydroxybutyrate) (PHB), the most studied PHA, has a molecular weight in the range of 10-3,000 kDa with a polydispersity of about 2, when produced from wild-type bacteria. Its glass transition temperature is near 180° C., and the densities of crystalline and amorphous PHB are 1.26 and 1.18 g/cm$^3$, respectively. Its mechanical properties (e.g., Young's modulus and tensile strength) are close to that of polypropylene though its extension to break is markedly lower than that of polypropylene.

Thus, PHAs offer an attractive alternative to commonly used synthetic biodegradable polymers.

A general structure of PHAs is presented in Formula I below, where the asterisks denote chiral centers (asymmetric carbons, when R differs from hydrogen):

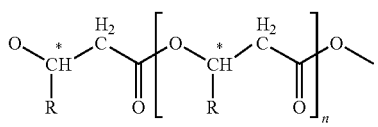

Formula I

Exemplary PHAs include poly(3-hydroxypropionate) (R=methyl), poly(3-hydroxybutyrate)(R=ethyl), poly(3-hydroxyvalerate)(R=propyl), poly(3-hydroxyhexanoate) (R=butyl), poly(3-hydroxyoxtanoate)(R=pentyl) and poly(3-hydroxydodecanoate)(R=nonyl).

Additional general features of PHAs characterization and biodegradation are described, for example, in Vert and Garreau [Clin Mater 1992; 10:3-8]; Seebach and Fritz [International Journal of Biological Macromolecules 1999:25:217-236]; Brandi et al. [Adv Biochem Eng Biotechnol 1990; 41:77-93]; Bonthrone et al. [FEMS Microbiol Rev 1992; 10:269-78]; and Mergaert et al. [FEMS Microbiol Rev 1992; 10:317-22].

Biodegradable polymers that have one or more stereogenic center(s) (namely, optically active polymers), offer advantageous features when used as carriers for drug delivery. Many biologically active molecules are optically active (chiral), and usually the biological activity can vary greatly depending on the optical purity of the molecule. Much research activity has been focused on the development of technologies allowing access to pure enantiomers. When serving as carriers of chiral (optically active) drugs, biodegradable polymers that have a pre-determined chirality can serve for forming a hetero-stereo complexes with a chiral drug, thus serving as an optically active delivery system.

Hetero-stereo complexation is a new concept in the interaction between complementary optically active polymeric chains which can be utilized for the delivery of, for example, peptides, proteins and other optically active macromolecules. Unlike common delivery systems where the drug powder is physically entrapped in a polymer matrix and the peptide is released by diffusion through the matrix, stereocomplexes form a stereospecific interaction between the optically active drug and the complementary polymer chain. The drug release under physiological conditions is by cleavage of the polymer chain, which reduces the interactions with the drug.

Recently, it has been shown that optically active polylactic acid (PLA)-based polymers form stable hetero-stereo complexes with various peptides. Slager and Domb reported heterocomplexation between D-PLA and L-configured peptides such as the luteinizing hormone-releasing hormone (LHRH) [Eur. J. Pharm. Biopharm. (2004) δ 461-469; Macromolecules (2003), 36, 2999-3000] leuproide (an LHRH nonapeptides analogue) [Biomacromolecules (2003), 4, 1308-1315], vapreotide a cyclic octapeptide somatostatin) analogue) [Advanced Drug Delivery Reviews 55 (2003) 549-583], insulin [Biomaterials 23 (2002) 4389-4396], lysozyme and somastatin [Journal of Controlled Release (2005) 107 (3) 474-483].

Furthermore, biodegradable polymers that have a pre-determined chirality can be used to enhance the permeation of the drug delivery system through various membranes. Thus, it has been reported, for example, that enantioselective transdermal permeation was observed with some chiral excipients, indicating that and t using chiral polymers as drug carriers may assure that only the active drug penetrates the skin [Reddy et al., *Crit. Rev Ther Drug Carrier Syst.* 2000; 17(4): 285-325)].

In addition, when biodegradable polymers are designed to biodegrade via enzymatic cleavage, the chirality of the polymer or of portions thereof, namely, L or D, plays a crucial role in the degradation process. Thus, portions of a biodegradable polymer which has a D chirality would be stable to enzymatic degradation, whereby portions of polymer which have L chirality would be readily susceptible to enzymatic degradation.

The beneficial effect of chiral biodegradable polymers, and the other advantages associated with polyesters in general, and PHAs in particular, have prompt many researchers to study the properties and synthesis of α-hydroxy carboxylic acids, the building blocks of these polymers.

There are numerous examples where the hydroxyl group at the α-position provides an internal control element, facilitating stereoselective transformations of a prochiral functional group. It has been found that chiral α-hydroxy carboxylic esters, acids and their salts, offer versatile synthetic intermediates for the synthesis of polyesters that contain additional chiral centers.

Although α-amino carboxylic acids (amino acids, AA) are considered relatively cheap reagents, there are only a few examples of traditional chemical methods that directly produce α-hydroxy-carboxylic acids or their salts from α-amino carboxylic acids or their salts. The main obstacles of such a transformation generally result from the use of water-sensitive reagents and low temperatures on extremely polar compounds at a relatively unreactive and stereochemically sensitive center.

Thus, for example, α-hydroxy carboxylic acids can be prepared using α-keto carboxylic acids or esters as starting materials. This methodology, however, is limited due to the non-chirality, high cost and limited availability of the starting materials. The chirality of the final product is often induced by a stoichiometric amount of a chiral auxiliary, requiring several synthetic steps and/or a bulky and costly chiral reductant.

Enantioselective reduction of enones can be achieved using a catalytic amount of a chiral oxazaborolidine [Coney, et. al. Tet. Lett., 1990, 31,611]. However, a sequence of chemical conversions are required in order to transform the initially formed chiral alcohol to a α-hydroxy ester with obvious cost and yield implications.

Enzymatic methods that produce chiral α-hydroxy-carboxylic acids have also been suggested. These methods utilize α-keto carboxylic esters or acids as precursors and involve catalysis by purified or isolated reductases [see, for example, U.S. Pat. Nos. 5,098,841; 4,326,031; and 5,686, 275).

WO 02/33110 discloses processes that utilize α-amino carboxylic acids or their salts as starting materials for the efficient and inexpensive production of α-hydroxy acids. This process involves the use of two enzymes: amino acid deaminases (AAD) along with lactate dehydrogenases (LAD). This patent application, however, fails to teach the use of hydroxy carboxylic acid for preparing biodegradable polyesters, and hence further fails to teach the provision of biodegradable polyesters while utilizing amino acids as the starting material.

The use of proteinaceous materials for producing biodegradable polymers has been recently disclosed in WO 04/50732. According to the teachings of WO 04/50732, primary amine and/or amide groups of a proteinaceous substrate are replaced by hydroxyl and/or carboxyl groups, respectively, and the resulting substrate is subjected to polymerization. The hydroxyl and carboxyl groups are introduced to the substrate by reaction with nitrous acid or nitrous oxides. The hydroxyl and carboxyl groups are introduced to the substrate by replacing amines and amides either at the N-terminus of the substrate or at a side chain thereof. Polymerization is thereafter effected via formation of esters bonds between hydroxyl and carboxyl groups. In preferred embodiments of this patent application, amine or amide groups at the side chain of peptides are replaced by hydroxyl or carboxyl groups and polycondensation is effected between two compatible side chains of two polymers, to thereby generate polyamides that are interlinked therebetween via polyester bonds. The conditions under which the modification of the proteinaceous material and the polymerization thereof are effected are relatively harsh and are not directed at maintaining the chirality of the proteinaceous substrate.

Furthermore, the functionality of the proteinaceous material is affected by utilizing its side chain for polymerization. WO 04/50732 therefore fails to teach processes of polymerizing proteinaceous materials while maintaining the original chirality and functionality of the pre-polymerized material upon polymerization.

Thus, there is a widely recognized need for, and it would be highly advantageous to have, novel processes of producing polymers, in particular polyhydroxyalkanoates, in which the chirality and functionality (e.g., side chain structure) of the pre-polymerized monomers forming the polymer, is maintained.

SUMMARY OF THE INVENTION

According to one aspect of the present invention there us provided a polymer comprising a plurality of monomer residues being linked to one another and forming a polymer backbone, at least a portion of the monomer residues comprises residues of at least one chiral pre-polymerized monomer, wherein a chirality of the chiral pre-polymerized monomer is maintained in the monomer residues in the polymer, and further wherein an asymmetric atom in the chiral pre-polymerized monomer forms a part of the backbone, with the proviso that the polymer is not a polypeptide.

According to further features in the preferred embodiments of the invention described below, the chiral pre-polymerized monomer is a derivative of a chiral amino acid.

According to still further features in the preferred embodiments of the invention the chiral amino acid is selected from the group consisting of a D-α-amino acid, an L-α-amino acid, a D-β-amino acid, and an L-β-amino acid.

According to still further features in the preferred embodiments of the invention the derivative of the chiral amino acid is selected from the group consisting of a α-hydroxy amino acid, a 2-alkyl-1,2-diol derivative of the amino acid and an aminoalcohol derivative of the amino acid.

According to still further features in the preferred embodiments of the invention each of the at least one chiral pre-polymerized monomer independently has the general Formula IIa or IIb:

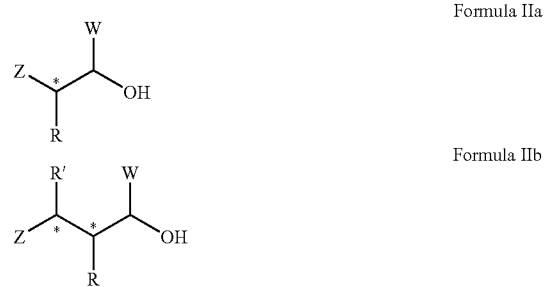

wherein:

each * independently denotes an R configuration or an S configuration; each of R and R' is independently selected from the group consisting of hydrogen, a positively charged moiety, a negatively charged moiety, a hydrophobic moiety, and a hydrophilic moiety, provided that at least of R and R' is not hydrogen; Z is selected from the group consisting of OH, SH and NH$_2$; and W is selected from the group consisting of =O and RaRb, whereas each of Ra and Rb is independently hydrogen or alkyl, with the proviso that the pre-polymerized monomer is not an amino acid.

According to still further features in the preferred embodiments of the invention at least one of R and R' is a side chain of an amino acid.

According to still further features in the preferred embodiments of the invention the polymer further comprises at least one monomer residue selected from the group consisting of an amino acid residue, a hydroxy carboxylic acid residue, a dialkylene glycol residue and a dicarboxylic acid residue.

According to still further features in the preferred embodiments of the invention the monomer residues are linked to one another by a bond selected from the group consisting of an ester bond and an amide bond.

According to still further features in the preferred embodiments of the invention the polymer is a biodegradable polymer.

According to still further features in the preferred embodiments of the invention the polymer has a molecular weight that ranges from about 1000 Da to about 50,000 Da.

According to another aspect of the present invention there is provided a process of preparing a polymer, the process comprising polymerizing at least one chiral pre-polymerized monomer to thereby form a polymer which comprises a plurality of monomer residues being linked to one another and forming a polymer backbone, at least a portion of the plurality of the monomer residues being monomer residues of the at least one chiral pre-polymerized monomer, wherein a chirality of the chiral pre-polymerized monomer is maintained in the monomer residues in the polymer, and further wherein an asymmetric atom in the chiral pre-polymerized monomer forms a part of the backbone, with the proviso that the polymer is not a polypeptide.

According to further features in the preferred embodiments of the invention described below, the polymerizing comprises condensing at least two of the chiral pre-polymerized monomers.

According to still further features in the preferred embodiments of the invention the process further comprises, prior to the polymerizing, cyclizing the at least one chiral pre-polymerized monomer to thereby provide a cyclic compound which comprises at least one residue of the at least one chiral pre-polymerized monomer.

According to still further features in the preferred embodiments of the invention the polymerizing comprises a ring opening polymerization.

According to still further features in the preferred embodiments of the invention the cyclizing is effected in the presence of ketone and the cyclic compound further comprises a residue of the ketone.

According to still further features in the preferred embodiments of the invention the polymerizing comprises an enzymatically-catalyzed polymerization.

According to still further features in the preferred embodiments of the invention the polymer consists essentially of the monomer residues of the at least one chiral pre-polymerized monomer, and the polymerizing comprises: conjugating at least two of the at least one chiral pre-polymerized monomers to one another, to thereby form at least one oligomer comprising the at least two residues of the at least one chiral pre-polymerized monomer being sequentially linked to one another; and polymerizing the at least one oligomer.

According to still further features in the preferred embodiments of the invention the polymer further comprises at least one residue of a hydroxy carboxylic acid, and the polymerizing comprises: conjugating the at least one chiral pre-polymerized monomer and the at least one hydroxy carboxylic acid, to thereby form at least one conjugate of a residue of the at least one chiral pre-polymerized monomer being linked to a residue the hydroxy carboxylic acid; and polymerizing the at least one conjugate.

According to still further features in the preferred embodiments of the invention the polymer further comprises at least one residue of a dicarboxylic acid, and the polymerizing comprises: conjugating the at least one chiral pre-polymerized monomer and the at least one dicarboxylic acid, to thereby form at least one conjugate of a residue of the at least one chiral pre-polymerized monomer being linked to a residue of the dicarboxylic acid; and polymerizing the at least one conjugate.

According to still further features in the preferred embodiments of the invention the at least one chiral pre-polymerized monomer is a derivative of a chiral amino acid.

According to still further features in the preferred embodiments of the invention derivative of the chiral amino acid is selected from the group consisting of a α-hydroxy amino acid, a 2-alkyl-1,2-diol derivative of the amino acid and an aminoalcohol derivative of the amino acid.

According to still further features in the preferred embodiments of the invention the derivative of the chiral amino acid is a α-hydroxy amino acid, the process further comprising, prior to the polymerizing, converting the chiral amino acid to the α-hydroxy amino acid, whereas the α-hydroxy amino acid maintains a chirality of the chiral amino acid.

According to still further features in the preferred embodiments of the invention the converting comprises reacting the chiral amino acid with a nitrite.

According to still further features in the preferred embodiments of the invention the converting comprises subjecting the chiral amino acid to an enzymatic catalysis, the enzymatic catalysis being effected by an amino deaminase and a lactate dehydrogenase.

According to still further features in the preferred embodiments of the invention the derivative of the chiral amino acid is a 2-alkyl-1,2-diol derivative of the amino acid, the process further comprising, prior to the polymerizing: converting the chiral amino acid to a α-hydroxy amino acid, whereas the α-hydroxy amino acid maintains a chirality of the chiral amino acid; and converting the α-hydroxy amino acid to the 2-alkyl-1,2-diol derivative of the amino acid, whereas the 2-alkyl-1,2-diol derivative of the amino acid maintains a chirality of the chiral amino acid.

According to still further features in the preferred embodiments of the invention the derivative of the chiral amino acid is an aminoalcohol derivative of the amino acid, the process further comprising, prior to the polymerizing, converting the chiral amino acid to the aminoalcohol derivative of the amino acid, whereas the aminoalcohol derivative of the amino acid maintains a chirality of the chiral amino acid.

According to still another aspect of the present invention there is provided a conjugate comprising the polymer described herein having attached thereto an active agent.

According to further features in the preferred embodiments of the invention described below, the active agent is selected from the group consisting of a therapeutically active agent, a labeling agent, a cross-linking agent and an additional polymer.

According to still further features in the preferred embodiments of the invention the active agent is a therapeutically active agent.

According to still further features in the preferred embodiments of the invention the active agent is a chiral active agent. In preferred embodiments, such agent forms a hetero-stereo complex with the polymer.

Hence, according to yet another aspect of the present invention there is provided a hetero-stereo complex comprising the polymer described herein having complexed thereto a chiral agent, the chiral agent having a stereoconfiguration suitable for forming a stereointeraction with the polymer. Preferably, the chiral agent is a chiral therapeutically active agent such as, but not limited to, a peptide, a protein and a chiral macromolecule.

According to an additional aspect of the present invention there is provided a pharmaceutical composition comprising the polymer described herein and a pharmaceutically acceptable carrier.

According to still an additional aspect of the present invention there is provided a use of the polymer described herein for the preparation of a medicament.

According to yet an additional aspect of the present invention there is provided a method of treating a medical condition in a subject in need thereof, the method comprising administering to the subject the polymer described herein.

According to a further aspect of the present invention there is provided a pharmaceutical composition comprising the conjugate described herein and a pharmaceutically acceptable carrier.

According to still a further aspect of the present invention there is provided a use of the conjugate described herein for the preparation of a medicament. The medicament can be for the treatment of a medical condition for which a therapeutically active agent attached to the polymer is beneficial or for delivering the therapeutically active agent to a targeted bodily site.

According to yet a further aspect of the present invention there is provided a method of slow-releasing an agent to an environment (e.g., a body of an organism), the method comprising contacting a conjugate which comprises the polymer described herein having the agent attached thereto, with the environment. Alternatively, the method comprising contacting a hetero-stereo complex which comprises the polymer described herein having complexed thereto the chiral agent, the chiral agent having a stereoconfiguration suitable for forming a stereointeraction with the polymer, with the environment.

According to an additional aspect of the present invention there is provided a method of a delivering a therapeutically active agent to a bodily organ of a subject in need thereof, the method comprising administering to the subject a therapeutically effective amount the conjugate described herein.

According to still an additional aspect of the present invention there is provided a method of treating a medical condition in a subject in need thereof, the method comprising administering to the subject a therapeutically effective amount of the conjugate or the hetero-stereo complex described herein, having a therapeutically active agent attached or complexed thereto, wherein the therapeutically active agent is beneficial in the treatment of the medical condition.

According to a further aspect of the present invention there is provided a medical device comprising any of the polymers and conjugates described herein.

The present invention successfully addresses the shortcomings of the presently known configurations by providing novel optically active polymers, having pre-determined chirality and other functional properties, prepared by utilizing cost-effective and available starting materials, which may serve as therapeutically active macromolecules per se, as novel carriers for delivering drugs, particularly optically active drugs, as well as substances for use in other medical or non-medical applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein the term "about" refers to ±10%.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
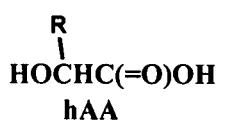
FIG. 1 presents schematic illustration of exemplary polymers according to preferred embodiments of the present invention.
Figure 1:
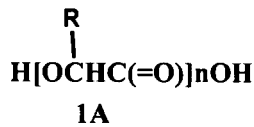
Figure 1:
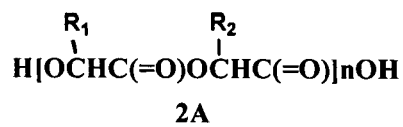
Figure 1:
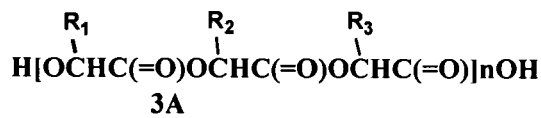
Figure 1:
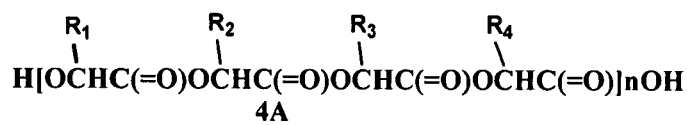
Figure 1:
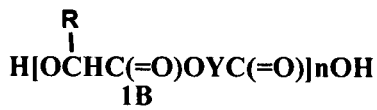
Figure 1:
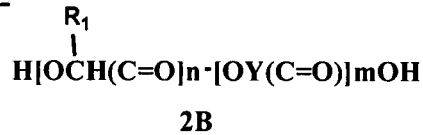
Figure 1:
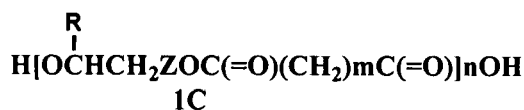
Figure 1:
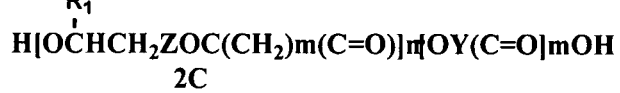
Figure 1:
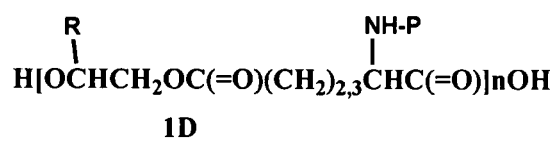

The present invention is of polymers that are composed of monomer residues derived from optically active (chiral) pre-polymerized monomers, which maintain the chirality of the pre-polymerized monomer upon polymerization and hence form optically active polymers. The polymers of the present invention can be composed of monomer residues that are derived from readily available chiral monomers and can be designed to have pre-determined characteristics such as chirality, biodegradability and functionality. The present invention is further of compositions containing and methods utilizing these polymers. The polymers according to the present invention can be used as therapeutically active agents per se, as carriers of therapeutically active agents, which can be used, for example, for delivering the active agents to a targeted bodily site and/or for a sustained release of the active agent, or in the constructions of medical devices and other articles-of-manufacture. The present invention is further of processes of preparing such polymers. The present invention is further of conjugates of these polymers and various agents and particularly of hetero-stereo complexes of these polymers and stereo-complementary macromolecules such as peptides and proteins.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In view of the evolving need for novel biodegradable polymers which have one or more stereogenic centers and can thus serve, for example, as efficient carriers for delivering optically active drugs, the present inventors have sought for an efficient, cost-effective route for providing such polymers. Thus, while conceiving the present invention, the present inventors have envisioned that utilizing amino acids as an available, diverse and cheap source for forming versatile building blocks of such polymers could pave the way for obtaining newly designed polymers that would exhibit the desired properties.

While reducing the present invention to practice, the present inventors have devised and successfully practiced a novel methodology for preparing optically active polymers, having a variety of pre-determined properties such as chirality, biodegradability, hydrophobicity/hydrophilicity and charge distribution. More specifically, the present inventors have devised a novel methodology for preparing a combinatorial library of thousands of polymers, particularly hydrolytically-cleavable polymers, each having a pre-determined profile. This methodology utilizes readily available starting materials such as amino acids, which are subjected to various modifications, while maintaining both their chirality and functionality, so as to provide a plurality of chiral, functional, building blocks. These building blocks can thereafter be subjected to various polymerization processes, which are also designed so as to maintain the chirality of the building blocks during the polymerization, to thereby provide optically active homopolymers, copolymers, branched polymers and cross-linked polymers, exhibiting various side-chain functionalities such as charge profile, hydrophobicity/hydrophilicity, reactivity and the likes.

Thus, according to one aspect of the present invention there is provided a polymer which comprises a plurality of monomer residues being linked to one another and forming a polymer backbone, whereby at least a portion of these monomer residues comprises residues of one or more chiral pre-polymerized monomer(s), wherein a chirality of these chiral pre-polymerized monomer is maintained in the monomer residues in the polymer. The chiral pre-polymerized monomers are selected such that an asymmetric atom in the chiral pre-polymerized monomer forms a part of the polymer backbone.

As used herein throughout, the term "monomer" describes a compound that can be subjected to a polymerization process to thereby form a polymer. The term "monomer" is therefore used herein to describe a building block of a polymer. Thus, the terms "building block" and the term "monomer" are used herein interchangeably.

The phrase "pre-polymerized monomer" is used herein to describe the monomeric compound prior to its polymerization. This phrase is used herein to distinct a pre-polymerized monomer from the monomer residue formed from the monomer upon its incorporation into a polymer by a polymerization process.

As used herein throughout, the term "residue" describes a major portion of a molecule that is linked to another molecule while maintaining its functionality.

The phrase "monomer residue" therefore describes a major portion of a monomeric compound that is present within a polymer upon polymerization. In other words, this phrase describes a residue of a polymer building block or building unit. This phrase actually describes a polymer building unit that is derived from the pre-polymerized monomer.

Thus, for example, the phrase "pre-polymerized monomer" is used herein to describe a monomeric compound that is polymerizable, namely, has one or more reactive groups that can be utilized to form covalent bonds with other, same or different, groups, via common polymerization processes. Such reactive groups include, for example, carboxylic groups, which can form ester bonds with hydroxyl groups, thioester bonds with thiols and amide bonds with amine or lactam groups; unsaturated groups (e.g., of olefins, dienes or acrylonitriles), which can form —C—C— bonds therebetween; and the like.

The phrase "monomer residue" is therefore used herein to describe that part in the polymer that is derived from a monomer upon its polymerization.

The phrases "monomer residue", "monomer unit", "building unit" and "building block unit" are used herein interchangeably.

The term "polymer" as used herein describes a large molecule that is made up of repeating units. The repeating units can all be the same (polymer) or different (co-polymer). The repeating units represent the polymer building units, which are also referred to herein, as described hereinabove, as monomer residues.

Polymers may be classified by their repeating unit structure and may be linear, branched or, less commonly, cyclic. Copolymers contain two or more different monomers that can be arranged randomly or in repeating sequence blocks in the polymeric structure. In solution, entangled polymer chains can create networks, giving complex viscosity behavior. Generally, the term "polymer" encompasses, but is not limited to, homopolymers, co-polymers, such as for example, block, graft, random and alternating co-polymers, ter-polymers, and blends and modifications thereof, of various molecular weights. Furthermore, unless otherwise specifically limited, the term "polymer" includes all possible stereochemical configurations and conformations of the molecule. These configurations and conformations include, but are not limited to, any combination of isotactic, syndiotactic and atactic, cis and trans, and R and S and conformations.

The term "chiral", as used herein, describes a property of a compound which renders the compound not superimposable on its mirror image.

The term "chiral" is also referred to herein and in the art as "optically active", a phrase which represents the interaction of chiral materials with polarized light. Thus, chiral materials cause rotation of the plane of polarization of a polarized light beam.

Chiral organic compounds typically has one or more asymmetric centers, namely, a tetrahedral atom that has four different groups attached thereto. The arrangement of these different groups around the asymmetric atom determines its optical activity. This arrangement is determined in the art by the terms S|R; D/L; (−)/(+) and the like.

Thus, the phrase "chiral pre-polymerized monomer" describes a chiral compound that has one or more asymmetric atoms, as defined herein. The asymmetric atoms can be carbon atoms, silicone atoms, tellurium atoms, selenium atoms and any other tetrahedral atoms. Preferably, the asymmetric atom is a carbon atom.

Each of the monomer residues in the polymer that are derived from chiral pre-polymerized monomers therefore includes one or more asymmetric atoms such as asymmetric carbon atoms. These monomer residues are constructed within the polymer such that at least one of these asymmetric atoms forms a part of the polymer backbone.

As used herein and in the art, the phrase "polymer backbone" describes the chain formed by the reaction between the reactive groups in the monomer that leads to the polymerization. The groups of the monomer units that do not participate in the polymerization reaction(s) are hanging from the polymer backbone and are referred to to as "polymer side chains".

Thus, the monomer residues that are derived from chiral pre-polymerized monomers are present in the polymer such that the asymmetric atom of the chiral monomer forms a part of the polymer backbone.

The term "chirality", as is well known in the art, describes the optical activity of a compound, as this phrase is defined herein. Thus, by the phrase "maintains a chirality" it is meant that a monomer residue within the polymer has the same chirality as that of the pre-polymerized monomer. For example, if a pre-polymerized monomer has an asymmetric atom with an S-configuration, the corresponding asymmetric atom in the monomer residue has the same configuration, namely, the same arrangement of the groups that are attached thereto and do not participate in the polymerization.

As used herein, the term "portion" describes a substantial part of the monomer residues constructing the polymer (in distinction from a single residue or, for example, from a few residues (e.g., 2, 3, 4, or 5) out of hundreds of residues). The term "portion" therefore describes, for example, about 10%, about 20%, about 30%, about 40% and even about 50% of the monomer residues composing the polymer.

Thus, the phrase "at least a portion" with respect to the plurality of monomer residues refers, for example, to at least 10%, at least 20%, at least 30%, at least 40%, at least 50%, at least 60%, at least 70%, at least 80%, at least 90% and even 100% of the monomer residues composing the polymer.

The phrase "plurality of monomer residues" describes three of more monomer residues.

Thus, the polymers described herein can comprise from 3 monomer residues and up to dozens, hundreds and even thousands monomer residues, depending on the intended use thereof.

The polymers described herein, however, are not polypeptides.

As used herein, the term "polypeptide" describes any peptide that is essentially composed of amino acid residues that are linked to one another via a peptide bond (namely, an amide, —NH—C(=O)—, bond). This term encompasses native peptides (either degradation products, synthetically synthesized peptides or recombinant peptides) and synthetically synthesized peptides.

As used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, modified amino acids such 2-aminoadipic acid, hydroxylysine, isodemosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which represent exemplary amino acids according to the various embodiments of the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |

TABLE 2-continued

| Non-conventional amino acid | Code | Non-conventional amino acid | Code |
|---|---|---|---|
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |

TABLE 2-continued

| Non-conventional amino acid | Code | Non-conventional amino acid | Code |
| --- | --- | --- | --- |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
|  | Nnbhm | N-(N-(3,3-diphenylpropyl) | Nnbhe |
| N-(N-(2,2-diphenylethyl) carbamylmethyl-glycine | Nnbhm | carbamylmethyl(1)glycine |  |
| 1-carboxy-1-(2,2-diphenyl ethylamino)cyclopropane | Nmbc |  |  |

Table 2 Cont.

Further excluded from the scope of the present invention are common non-peptidic polymers that are characterized by a pre-determined portion of monomer residue that are derived from chiral per-polymerized monomers, such as, for example, D- and L-polylactic acid. It should be noted, however, that building blocks of such polymers can be utilized for constructing the polymer according to the present embodiments, in addition to the chiral monomers described herein. Such polymers can be further included within the polymer as a co-polymer or block polymer, in addition to the portion of the polymer described herein, as is detailed hereinunder.

The polymers described herein are therefore composed of a plurality of monomer residues, as described herein, whereby at least a portion of these monomer residues are derived from chiral monomers and maintain the same chirality as that of the pre-polymerized monomer. The polymers described herein are therefore optically active polymers having a number of stereogenic centers in their backbone.

As used herein, the phrase "stereogenic center" describes a atom within the polymer backbone, as defined herein, that is derived from an asymmetric atom of a pre-polymerized chiral monomer that is utilized for constructing the polymer.

In cases where the polymer includes one or more residues other that those derived from chiral monomers, these other residues can derive either from chiral or non-chiral monomers.

The chiral monomers utilized for forming portion(s) of the polymer described herein can be any compound that can be subjected to polymerization while maintaining the chirality of the monomers, such that an asymmetric atom in the chiral monomer forms a part of the polymer backbone.

Considering the advantages of optically active polymers that are biodegradable, discussed hereinabove, while devising the novel methodology described herein, the present inventors have focused on such polymers that are biodegradable.

Thus, according to preferred embodiments of the present invention, the polymers described herein are biodegradable polymers.

The term "biodegradable" as used in the context of the present invention, describes a material which can decompose under physiological conditions into breakdown products. Such physiological conditions include, for example, hydrolysis (decomposition via hydrolytic cleavage), enzymatic catalysis (enzymatic degradation), and mechanical interactions.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

The term "biodegradable polymer", as used herein, refers to a polymer that at least a portion thereof, as defined hereinabove, decomposes under physiological conditions. The polymer can thus be partially decomposed or fully decomposed under physiological conditions.

The biodegradability of polymers is often determined by the type of linkages (bonds) linking the building units (monomer residues) of the polymer. Linkages that readily undergo hydrolysis or enzymatic cleavage contribute to high degree and/or relatively fast of biodegradability (namely, polymer degradation into break-down decomposition products), whereby linkages that are more stable to these reactions contribute to low degree and/or slow biodegradability and even to complete stability of the polymer in terms of its biodegradability. By controlling the type of linkages throughout a polymer, the decomposition degree and decomposition products of the polymer can be determined.

Thus, according to preferred embodiments of the present invention, at least a portion of the monomer residues composing the polymer are linked to one another via a biodegradable bond.

The phrase "biodegradable bond" is used herein to describe a bond that can be cleaved under physiological conditions. Cleavage can be by a chemical reaction (e.g., hydrolysis) or by enzymatically catalyzed reaction.

Representative examples include ester bonds and amide bonds, as these terms are defined hereinbelow.

As used herein, the phrase "ester bond" encompasses a carboxylic ester bond (—O—C(=O)—), a thiocarboxylic ester bond (—O—C(=S)—) and a thiocarboxylic thioester bond (—S—C(=S)—).

As used herein, the phrase "amide bond" encompasses both a carboxylic to amide bond (—NRx—C(=O)—), and thiocarboxylic amide bond (—NRx—C(=S)—), where Rx can be hydrogen, alkyl, cycloalkyl or aryl, as defined herein.

In preferred embodiments of the present invention, at least a portion of the monomer residues composing the polymer described herein are linked to other monomer residues via carboxylic ester bonds. In one preferred embodiment, all of the monomer residues composing the polymer described herein are linked to one another via carboxylic ester bonds, thus forming a polyester. In other preferred embodiments, the monomer residues composing the polymer described herein are linked to other monomer residues via a combination of carboxylic ester bonds and carboxylic amide bonds, thus forming a polyester having interdispersed therewithin amide bonds.

While, as discussed hereinabove, the present inventors have sought for polymers that would be derived from cheap and readily available starting materials, in a preferred embodiment of the present invention, the chiral pre-polymerized monomer is a derivative of a chiral amino acid.

As defined hereinabove, the phrase "amino acid", as used herein, describes both naturally-occurring amino acids and modified amino acids, representative examples of which are presented in Tables 1 and 2 above, respectively. This phrase therefore encompasses, for example, D-α-amino acids, L-α-amino acids, D-β-amino acids, and L-β-amino acids.

Amino acids are readily available, relatively cheap, and yet non-toxic substances and are therefore highly beneficial for use as starting materials for constructing the polymers described herein.

Amino acids further offer a wide variety of functionalities that can be attributed to the polymer properties. The variety and versatility of side chains of available amino acids presents a wide range of functionalities including, for example, hydrophobicity, hydrophilicity, positive charge, negative charge, chirality and reactivity groups for attaching various agents. Thus, by selecting monomers that are derived from amino acids, a myriad of properties of the polymer resulting from these monomers can be pre-determined, including, for example, the hydrophobicity/hydrophilicity/amphiphility of the polymer and as a result its stearic arrangement; the net positive charge of the polymer and as a result its cell permeability and/or other targeting properties; the chirality of the polymer, namely, D-configuration, L-configuration or combinations thereof, and as a result its susceptibility to enzymatic cleavage, and its capability of interacting with agents such as therapeutically active agents, labeling moieties, cross-linking agents and the like, as is detailed hereinbelow.

Furthermore, by utilizing amino acid derivatives as building units of the polymer, desired non-toxic, water soluble decomposition products (e.g., amino acids or short peptides) are formed upon biodegradation of the polymer.

As used herein, the term "derivative" describes a compound that has been subjected to one or more chemical modifications, preferably while maintaining the majority of its functionalities and structural features. Such chemical modifications includes, for example, substitution, oxidation, reduction, and the like.

Preferably, the chiral amino acid derivative utilized for forming the polymer described herein, has the same chirality as that of the amino acid from which it is derived.

As is well-known in the art, the chirality of an amino acid is derived from the asymmetry of the Cα-carbon. In β-amino acids, the chirality can be derived from the asymmetry of at least one or both of the Cα-carbon and/or the Cβ-carbon.

When the monomers utilized for constructing the polymer are chiral amino acid derivatives, the asymmetric Cα-carbons and/or the Cβ-carbons form the polymer backbone.

As is demonstrated in the Examples section that follows and is further detailed hereinunder, the present inventors have successfully utilized various methodologies for producing derivatives of chiral amino acids while maintaining the chirality of the amino acid starting material. Using these methodologies, derivatives of chiral amino acid such as α-hydroxy amino acids, 2-alkyl-1,2-diol derivatives of said amino acid and aminoalcohol derivatives of amino acids have been prepared and successfully utilized as chiral monomers for constructing the polymers described herein.

As used herein, the phrase "α-hydroxy amino acid" describes an amino acid, as defined herein, in which the α-amine group in an α-amino acid and the β-amine group in a β-amino acid is replaced by a hydroxyl group. This phrase, further encompasses an amino acid, as defined herein, in which the α-amine or β-amine group is replaced by a thiohydroxy(thiol) group. α-Hydroxy amino acids are also referred to herein and in the art as glycolic acids.

The phrase "2-alkyl-1,2-diol derivative of amino acid" describes an α-hydroxy amino acid, as defined hereinabove, in which the α-carboxylate group is replaced by a —CH$_2$OH group.

The phrase "aminoalcohol derivatives of amino acid" describes an amino acid, as defined herein, in which the α-carboxylate group is replaced by a —CH$_2$OH group.

Thus, preferred chiral pre-polymerized monomers for use in the context of the present invention can be represented by the general Formulae IIa or IIb:

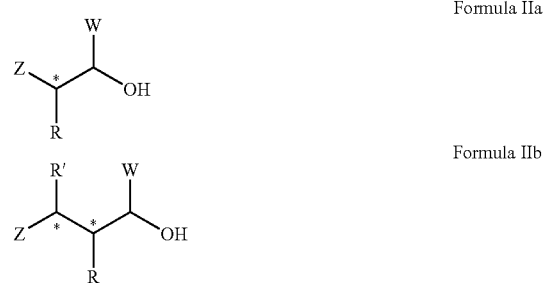

wherein:

each * independently denotes an R configuration or an S configuration;

each of R and R' is independently selected from the group consisting of hydrogen, a positively charged moiety, a negatively charged moiety, a hydrophobic moiety, and a hydrophilic moiety, provided that at least of R and R' is not hydrogen;

Z is selected from the group consisting of OH, SH and NH$_2$; and

W is selected from the group consisting of =O and RaRb, whereas each of Ra and Rb is independently hydrogen or alkyl, with the proviso the pre-polymerized monomer is not an amino acid. Lactic acid is included within the scope of this embodiment of the present invention, as long as it is not the only chiral monomer used for constructing the polymer.

When Z is OH or SH, the monomer is an α-hydroxy amino acid or a thiol derivative thereof.

When W is =O, the monomer is an α-hydroxy amino acid or a thiol derivative thereof. When W is RaRb, the monomer is either a 2-alkyl-1,2-diol derivative of an amino acid or an aminoalcohol derivative of an amino acid.

As used herein, the term "moiety" describes a chemical moiety or group that forms a part of a compound.

The phrase "hydrophobic moiety" describes a chemical moiety or group that has a minor or no affinity to water, that is, which has a low or no dissolvability in water and often in other polar solvents. Exemplary suitable hydrophobic moieties for use in the context of the present invention, include, without limitation, hydrophobic moieties that consist predominantly of one or more hydrocarbon chains and/or aromatic rings, and one or more functional groups which may be non-hydrophobic, but do not alter the overall hydrophobicity of the hydrophobic moiety. Representative examples include, without limitation, alkanes, alkenes, aryls and the likes, as these terms are defined herein, and any combination thereof.

The phrase "hydrophilic moiety" describes a chemical moiety or group that has high affinity to water, that is, which has relatively high dissolvability in water and often in other polar solvents. Exemplary suitable hydrophilic moieties for use in the context of the present invention, include, without limitation, hydrophilic moieties that include one or more atoms or groups that have high affinity to a water molecule, including, for example, amines, hydroxyls, thiols, carboxylates, phosphates, sulfates, phosphonates, sulfonates, diols and the like, as defined herein, provided that the moiety does not include a large hydrophobic group that masks the hydrophilic nature of such as group.

The phrases "negatively charged moiety" and "positively charged moiety", as used herein, refer to an ionizable group or moiety, which upon ionization, typically in an aqueous medium, has at least one negative or positive charge, respectively. The charged groups can be present in the monomers, monomer residues or polymers described herein either in their ionized form or as a pre-ionized form. Representative examples include, without limitation, amine, guanidine and imidazole, for positively charges groups and carboxylate, amide and hydroxyl for negatively charged groups.

As discussed hereinabove, these versatile moieties are preferably derived from the versatile side chains of amino acids. Thus, preferably, R in Formulae IIa and IIb above is a side chain of an amino acid and hence can be, for example, —(CH$_2$)$_3$—NH—C(NH$_2$)(=NH) (arginine side group), —(CH$_2$)$_4$NH$_2$ (lysine side group), —CH$_2$OH (serine side group), —CHOHCH$_3$ (threonine side group), —CH$_2$—C$_6$H$_4$p-OH (tyrosine side group), —CH$_2$CONH$_2$ (aspargine side group), —CH$_2$COOH (aspartic acid side group), —(CH$_2$)$_2$CONH$_2$ (glutamine side group), —(CH$_2$)$_2$COOH (glutamic acid side group), —CH$_2$SH (cysteine side group), —H (glycine side group), —CH$_3$ (alanine side group), —CH$_2$C(C=CH—N=CH—NH—) (histidine side group), —CH(CH$_3$)CH$_2$CH$_3$ (isoleucine side group), —CH$_2$CH(CH$_3$)$_2$ (leucine side group), —(CH$_2$)$_2$SCH$_3$ (methionine side group), —CH$_2$C$_6$H$_5$ (phenylalanine side group, —CH$_2$—C(C=CH—NH-Ph-) (tryptophan side group), and —CH(CH$_3$)$_2$ (valine side group).

Thus, for example, hydrophobic moieties can be derived from alanine, valine, leucine, isoleucine, phenylalanine, tryptophan and modifications thereof.

Positively charged moieties can be derived, for example, from lysine, arginine, histidine, and modifications thereof such as, for example, ornithine, 2,3,-diaminopropionic acid, 2,4-diaminobutyric acid, 2,5,6-triaminohexanoic acid, 2-amino-4-guanidinobutanoic acid, and homoarginine.

Negatively charged moieties can be derived, for example, from aspartate and glutamate and modifications thereof.

The degree of the above properties, e.g., hydrophobicity and charge, attributed by the side chains of the pre-polymerized monomers, can further be controlled by selecting, for example, amino acids with a certain degree of, for example, hydrophobicity or charge. Thus, for example, the hydrophobicity of tryptophan is higher than phenylalanine, which in turn, is higher than that of leucine. The positive charge of lysine is higher than histidine; and the negative charge of aspartate is higher than glutamate.

In addition, the selected side chains can attribute a functional reactivity to the polymer, by containing a reactive group.

As used herein, the phrase "reactive group" describes a chemical group that is capable of undergoing a chemical reaction that leads to a bond formation. The bond can be a hydrogen bond, an electrostatic bond, a covalent bond and the like. The reactive groups within the polymer can be utilized for forming a bond with, for example, a therapeutically active agent, a labeling moiety, a cross-linking agent, another polymer, and the like, as is detailed hereinbelow.

As is detailed hereinabove and is further discussed hereinbelow, by selecting the amino acids from which the chiral pre-polymerized monomer is derived and the sequence thereof within the polymer backbone, versatile properties of the polymer or of portions thereof can be pre-determined, by simply utilizing readily available starting materials.

In addition to the monomer residues deriving from the chiral per-polymerized monomers described herein, the polymer can further comprises other, chiral or non-chiral, monomer residues. These monomer residues can be derived from pre-polymerized polymers that may form biodegradable bonds, as is delineated hereinabove. Alternatively, these monomer residues can be derived from pre-polymerized monomers that form relatively stable bonds under physiological conditions and thus can form non-degradable portions within the polymer. Thus, the biodegradability of the polymer and/or portions thereof can be further pre-determined.

Considering the preferred pre-polymerized monomers according to the present embodiments, described herein, the other monomers within the polymer, if present, are selected capable of forming linkages with such pre-polymerized monomers, preferably under conditions that would not affect the optical activity of the polymer.

Examples of such additional pre-polymerized monomers include, without limitation, amino acids, hydroxy carbocylic acids, dicarboxylic acids and dialkylene glycols.

As used herein the phrase "hydroxy carboxylic acid" describes a HO-A-C(=O)OH, where A is alkyl, cycloalkyl or aryl, as defined herein.

The phrase "dicarboxylic acid" describes a HOC(=O)-A-C(=O)OH, where A is alkyl, cycloalkyl or aryl, as defined herein. In one embodiment, A is an alkyl, preferably a substituted alkyl and more preferably an alkyl substituted by an amine. According to this embodiment, the dicarboxylic acid can be an amino acid such as, for example, aspartate.

The phrase "dialkylene glycol" describes a OH-A-OH, where A is as defined herein.

Thus, as is further exemplified in the Examples section that follows, according to preferred embodiments of the present invention the polymer described herein essentially comprises monomer residues of a derivative of a chiral amino acid as described herein. Such a polymer can comprise, for example, repetitive units of one or more building units, whereby the building unit can be composed of one or more monomer residues of derivatives of chiral amino acid. Preferably, such a building block comprises from 1 to 10 monomer residues, more preferably from 1 to 6 and more preferably from 1 to 4 residues.

Further according to preferred embodiments of the present invention the polymer described herein comprises monomer residues of a derivative of a chiral amino acid and monomer residues of a hydroxy carboxylic acid. The hydroxy carboxylic acid can be chiral or non-chiral, aliphatic, alicyclic or aromatic and can further be substituted by various side chain, whereby all these features may further determine the properties of portions of the polymer. One or more hydroxy carboxylic acid residues can form, together with one or more monomer residues of a derivative of a chiral amino acid, a repetitive building unit in the polymer. Alternatively, the polymer can comprise block co-polymers, each comprising a different type of residues.

Further according to preferred embodiments of the present invention the polymer described herein comprises monomer residues of a derivative of a chiral amino acid and monomer residues of a dicarboxylic acid. The dicarboxylic acid can be chiral or non-chiral, aliphatic, alicyclic or aromatic and can further be substituted by various side chains, whereby all these features may further determine the properties of portions of the polymer. One or more dicarboxylic acid residues can form, together with one or more monomer residues of a derivative of a chiral amino acid, a repetitive building unit in the polymer.

Further according to preferred embodiments of the present invention the polymer described herein comprises monomer residues of a derivative of a chiral amino acid and monomer residues of an alkylene glycol. The alkylene glycol can be chiral or non-chiral, aliphatic, alicyclic or aromatic and can further be substituted by various side chains, whereby all these features may further determine the properties of portions of the polymer. One or more alkylene glycol residues can form, together with one or more monomer residues of a derivative of a chiral amino acid, a repetitive building unit in the polymer. Alternatively, the polymer can comprise block co-polymers, each comprising a different type of residues.

Further according to preferred embodiments of the present invention the polymer described herein comprises monomer residues of a derivative of a chiral amino acid, and two or more of monomer residues of an amino acid, a hydroxy carboxylic acid, a dicarboxylic acid and an alkylene glycol, according to the features outlined hereinabove.

As used herein throughout, the term "alkyl" refers to a saturated aliphatic hydrocarbon including straight chain and/or branched chain groups. Preferably, the alkyl group is a medium size alkyl having 1 to 10 carbon atoms. More preferably, it is a lower alkyl having 1 to 6 carbon atoms. Most preferably it is an alkyl having 1 to 4 carbon atoms. Representative examples of an alkyl group are methyl, ethyl, propyl, isopropyl, butyl, tert-butyl, pentyl and hexyl.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane.

The term "aryl" refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl.

The term "heteroaryl" includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heterocycloalkyl" refers to a monocyclic or fused ring group having in the ring(s) one or more atoms such as nitrogen, oxygen and sulfur. The rings may also have one or more double bonds. However, the rings do not have a completely conjugated pi-electron system.

Each of the alkyls, cycloalkyl, aryls, heteroaryls and heterocycloalkyls described herein can be further substituted. When substituted, the substituent group may be, for example, halogen, alkyl, alkenyl, alkynyl, cycloalkyl, aryl, heteroaryl, ehterocycloalkyl, alkoxy, aryloxy, thioalkoxy, thioaryloxy, nitro, cyano, trihalomethyl, alkylamino, sulfate, sulfonate, phoaphate, phosphonate, sulfinyl, phosphinyl, amine, amide, carbamyl, thioamide, thiocarbamyl, carboxylate, and thiocarboxylate.

As used herein, the term "alkenyl" describes an alkyl, as defined herein, which have at least two carbon atoms and at one double bond.

As used herein, the term "alkynyl" describes an alkyl, as defined herein, which have at least two carbon atoms and at one triple bond.

As used herein, the terms "hydroxy" and "hydroxyl" refers to an —OH group.

The terms "thiohydroxy", "thiohydroxyl" and "thiol" refers to a —SH group.

The term "alkoxy" refers to both an —O-alkyl and an —O-cycloalkyl group, as defined hereinbelow. Representative examples of alkoxy groups include methoxy, ethoxy, propoxy and tert-butoxy.

The term "thioalkoxy" refers to both a —S-alkyl and a —S-cycloalkyl group, as defined hereinabove.

The term "aryloxy" refers to both an —O-aryl and an —O-heteroaryl group, as defined herein.

A "thioaryloxy" group refers to both an —S-aryl and an —S-heteroaryl group, as defined herein.

As used herein, the term "halo" refers to a fluorine, chlorine, bromine or iodine atom.

The term "trihalomethyl" refers to a —$CX_3$ group, wherein X is halo as defined herein. A representative example of a trihalomethyl group is a —$CF_3$ group.

The term "amino" or "amine" refers to an —NR'R" group, where R' and R" are each independently hydrogen, alkyl or cycloalkyl, as is defined hereinabove.

The term "cyclic alkylamino" refers to an —NR'R" group where R' and R" form a cycloalkyl.

The term "nitro" refers to a —$NO_2$ group.

The term "cyano" or "nitrile" refers to a group.

The term "amide" refers to a —C(=O)—NR'R" group or to a —NR'—C(=O)—R", where R' and R" are as described hereinabove.

The term "carboxylate" refers to a —C(=O)—OR' group, where R' is as defined hereinabove.

The term "sulfate" refers to a "—$S(=O)_2OR'$ group, where R' is as defined hereinabove.

The terms "sulfonyl" and "sulfonate" refer to an —$S(=O)_2$—R' group, where R' is as defined herein.

The term "sulfinyl" refers to an —S(=O)R' group, where R' is as defined hereinabove.

The term "phosphonate" refers to a —P(=O)(OH)$_2$ group.

The term "phosphate" refers to an —O—P(=O)(OR')(OR") group, where R' and R" are as defined hereinabove.

The term "phosphinyl" refers to a —PR'R"R'" group, where R' and R" are as defined herein and R'" is defined for R'.

The term "guanidine" describes an —R'NC(=NR"")—NR"R'" group, where R', R" and R' are as defined herein and R"" is defined as either R', R" or R'".

The polymers described herein are designed so as to have a wide range of molecular weights, which can be further pre-determined while selecting the pre-polymerized monomers. Thus, each of the polymers described herein can a molecular weight that ranges from about 1,000 Da to about 50,000 Da.

Apart for properties such as chirality, biodegradability and functionality (in terms of charge, hydrophobicity/hydrophilicity and reactivity), other properties of the polymer which can be pre-determined by selecting the polymer's composition. These include, for example, melting point, crystanility, mechanical strength and modulus.

Thus, for example, the polymers described herein can be pre-determined so as to have a melting point that ranges from about 50° C. and about 200° C. based on the nature of the side groups. Side groups that contain a phenyl group have high melting point while non-linear aliphatic side groups such as isopropyl or isobutyl may result is low meting polymers.

Furthermore, the crystallinity of the polymer can be determined, for example, by the chiral building blocks used. Homopolymers composed of one enantiomers are stereo-regular polymers that exhibit high crystallinity and mechanical strength. Copolymers are less crystalline compared to the stereoregular homopolymers.

As mentioned hereinabove, a unique methodology has been developed for preparing the polymers described herein. Thus, according to another aspect of the present invention there is provided a process of preparing a polymer, as described herein. The process comprises polymerizing at least one chiral pre-polymerized monomer to thereby form a polymer which comprises a plurality of monomer residues being linked to one another and forming a polymer backbone, whereby at least a portion of the plurality of the monomer residues are monomer residues of the at least one chiral pre-polymerized monomer. The polymerization is effected such that the chirality of the chiral pre-polymerized monomer is maintained in the monomer residues in the polymer, and further such that an asymmetric atom in the chiral pre-polymerized monomer forms a part of the backbone.

Thus, the process described herein is effected by polymerizing one or more chiral monomers, while maintaining the chirality of these monomers upon polymerization.

The polymerization can be effected either chemically or enzymatically.

Chemical polymerization of the chiral monomers can be effected, for example, by polycondensation. Thus, using known polycondensation procedures, homopolymers and/or bulk co-polymers are produced. The condensation can be performed in a bulk or in a solution, or, alternatively, involves conversion of the monomers to a reactive derivative thereof.

As mentioned hereinabove, preferred monomers according to the present embodiments are derived from amino acids. Reactive derivatives of amino acids can therefore be, for example, acyl halides, anhydrides, and the like, preferably acyl chloride.

The polycondensation can be further effected by means of a microwave, as id detailed in the Examples section that follows.

Alternatively, the chemical polymerization is effected by intercyclization of the monomer, to thereby form a cyclic intermediate, which can thereafter be subjected to ring opening polymerization (ROP). The cyclization of the monomer can be effected by reacting, in the presence of a suitable catalyst, two molecules of the same monomer or, by reacting molecules of different monomers. Depending on the structure of the monomer used, the intermediate cyclic compound can be, for example, a lactide, formed by cyclizing two α-hydroxy amino acids, or a cyclic compound formed by cyclizing an α-hydroxy amino acid and an amino acid.

Depending on the structure of the cyclic compound formed, the subsequent ROP can be effected in the presence of a suitable catalyst. Examples of suitable catalysts are presented in the Examples section that follows. When lactide is formed as the cyclic compound, the ROP can optionally be performed without a catalyst.

Further alternatively, the cyclization is effected between a chiral pre-polymerized monomer as described herein and a ketone. This cyclization utilizes the difunctionality of the monomer, to thereby produce an acetal-like structure, in which the ketone is interacted with the two functional moieties of the monomer. Polymerization of such a cyclic intermediate can be effected, for example, by a cationic, anionic or coordination catalysis, using, for example, nucleophilic, electrophilic or complexation catalysts, respectively. In a preferred embodiment, the polymerization of such a cyclic intermediate is effected in the presence of a nucleophilic catalyst, as depicted in the Examples section that follows.

Enzymatically-catalyzed polymerization can be performed, for example, by a lipase. Such a polymerization is preferably carried out in a non-aqueous medium.

The above polymerization techniques can be applied so as to polymerize various building blocks, to thereby obtain a desired polymer. As discussed hereinabove, the polymers prepared according the methodology described herein are characterized by pre-determined properties, which can be selected upon the intended use of the polymer. As is further discussed hereinabove, additional monomers that can be utilized for constructing the polymer include, for example, amino acids, hydroxy carboxylic acids, dicarboxylic acids, dialkylene glycols and combinations thereof.

In one embodiment, the polymer consists essentially of monomer residues of chiral pre-polymerized monomer, and the polymerization is effected by conjugating at least two of the chiral pre-polymerized monomers to one another, to thereby form one or more oligomer(s) comprising these residues of s chiral pre-polymerized monomer being sequentially linked to one another; and polymerizing the oligomer(s), using the methodologies described hereinabove. Thus, according to this embodiment, various building blocks, each being composed of the same or different pre-polymerized polymers, and each building block comprising one or more types of pre-polymerized monomer are first prepared.

Preferably, the sequence of the monomer residues in the oligomers is pre-determined. The oligomers can be prepared, for example, by solid phase synthesis, using common techniques, or in solution. Each oligomer preferably comprises from 1-10 monomer residues, more preferably from 1 to 6 monomer residues and more preferably from 1 to 4 monomer residues.

In another embodiment, the polymer further comprises residues of a hydroxy carboxylic acid, and the polymerization is effected by conjugating the chiral pre-polymerized monomer and the hydroxy carboxylic acid, and polymerizing the resulting conjugate, using the methodologies described hereinabove.

In yet another embodiment, the polymer further comprises residues of a dicarboxylic acid, and the polymerization is effected by conjugating the chiral pre-polymerized monomer and the dicarboxylic acid, and polymerizing the resulting conjugate, using the methodologies described hereinabove.

According to other embodiments of this aspect of the present invention, block co-polymers of each of the various monomers that are utilized for constructing the polymer are prepared, using the methodologies described hereinabove, and are thereafter linked together, in a pre-determined manner.

The utilized polymerization technique can further affect certain features of the obtained polymer. Thus, for example, polycondensation of the monomers or building blocks typically results in polymers having lower molecular weight, whereby polymerization by ring opening polymerization typically results in controllable, relatively high molecular weight of the polymer.

As is further discussed hereinabove, preferred chiral pre-polymerized monomers that can be beneficially utilized for constructing the polymer are derivatives of chiral amino acids such as, for example, α-hydroxy amino acids, 2-alkyl-1,2-diol derivatives of amino acid and aminoalcohol derivatives of amino acid.

The present inventors have utilized known methodologies for preparing various derivatives of chiral amino acids, while maintaining the chirality of the amino acid. However, unlike these known methodologies, the present inventors have utilized the obtained derivatives of chiral amino acids for constructing optically active polymers, which have pre-determined properties and can thus be used in a variety of applications, as is detailed hereinbelow.

In one embodiment, in cases where the derivative of a chiral amino acid is an α-hydroxy amino acid, the process further comprises, prior to the polymerization, converting the chiral amino acid to the α-hydroxy amino acid derivative thereof, whereby the α-hydroxy amino acid maintains a chirality of the chiral amino acid.

Converting the chiral amino acid to the α-hydroxy amino acid derivative thereof, according to this embodiment, can be effected by reacting the chiral amino acid with a nitrite (e.g., sodium nitrite). This reaction is preferably performed under conditions that maintain the chirality of the amino acid during the conversion and the product isolation. Further details are provided in the Examples section that follows.

Alternatively, converting the chiral amino acid to the α-hydroxy amino acid derivative thereof, according to this embodiment, can be effected by subjecting the chiral amino acid to an enzymatic catalysis. Such an enzymatic catalysis can typically be used for L-amino acids. Preferably, the enzymatic catalysis involves an enzymatic transformation that results in highly enantiomerically pure R- or S-isomers. The transformation is catalyzed by a coupled enzyme system of an amino acid deaminase (AAD), also referred to as amino acid oxidase (AAO), a lactate dehydrogenase (LDH) or *Saccharomyces* cerevsiae, an electron donor, and an enzyme/substrate system for recycling the electron donor. Additional details can be found in WO 02/33110.

In another embodiment, in cases where the derivative of the chiral amino acid is a 2-alkyl-1,2-diol derivative of the amino acid, the process further comprises, prior to the polymerization, converting the chiral amino acid to a corresponding α-hydroxy amino acid, as described hereinabove, and converting the α-hydroxy amino acid to the corresponding 2-alkyl-1,2-diol derivative of the amino acid. These conversions are effected such that the 2-alkyl-1,2-diol derivative maintains the chirality of the chiral amino acid utilized as the starting material.

Preferably, the 2-alkyl-1,2-diol derivative is obtained by subjecting the α-hydroxy amino acid to a reduction, by a reduction system that contains sodium borohydride and iodine.

In another embodiment, in cases where the derivative of the chiral amino acid is an aminoalcohol derivative of the amino acid, the process further comprises, prior to the polymerization, converting the chiral amino acid to a corresponding aminoalcohol derivative of the amino acid. This conversion is effected such that the aminoalcohol derivative maintains the chirality of the chiral amino acid utilized as the starting material.

Preferably, the aminoalcohol is obtained by subjecting the chiral amino acid to a reduction, by a reduction system that contains sodium borohydride and iodine.

As mentioned hereinabove, by pre-determining the sequence and chirality of the monomer residues within the polymer, and by utilizing monomer residues that are derived from derivatives of chiral amino acids, polymers that exhibit various pharmacological activities can be prepared. Thus, for example, polymers having a structure and composition of a depsipeptide can be utilized as anti-cancer, anti-viral, anti-bacterial, anti-fungal and/or anti-inflammatory agents. Similarly, polymers prepared after the sequence and chirality of other therapeutically active peptides can be prepared.

The composition and sequence of the chiral pre-polymerized monomers utilized for constructing the polymers presented herein can therefore be selected so as to exert a therapeutic effect per se, namely the polymers presented herein can act as therapeutically active agents by themselves.

Thus, according to an additional aspect of the present invention, there is provided a method of treating a medical condition in a subject in need thereof, which is effected by administering to the subject the polymer presented herein.

As used herein, the term "treating" includes abrogating, substantially inhibiting, slowing or reversing the progression of a medical condition, substantially ameliorating clinical or aesthetical symptoms of a medical condition or substantially preventing the appearance of clinical or aesthetical symptoms of a medical condition.

As used herein, the term "preventing" includes barring an organism from acquiring a medical condition in the first place.

The method, according to this aspect of the present invention, may further be effected by co-administering to the subject, in combination with the polymer presented herein, an additional therapeutically active agent which is beneficial in the treatment of the medical condition, as this is defined and discussed hereinabove.

For example, the polymers of the present invention, alone or in combination with any other therapeutically active agents, can be designed and utilized to destroy pathological microorganisms. The destruction of a pathogenic microorganism is effected by selectively destructing a portion of the cells of a pathogenic microorganism. While most known antibiotics act by interfering selectively with the biosynthesis of one or more of the molecular constituents of the cell-membrane, proteins or nucleic acids, the polymers described herein can be designed to act by binding and disrupting the outer membrane of the pathogenic microorganism cells. Disrupting the outer membrane of a cell causes its death due to membrane depolarization, leakage of metabolites and/or total loss of cell integrity; therefore the polymers of the present invention can also be designed to act directly as effective antimicrobial agents by disrupting the metabolism and/or the multiplication processes of the pathogenic microorganism.

The polymers described herein can also be designed to act synergistically with another antibiotic or other therapeutically active agent by permeabilizing the cells of the pathogenic microorganism; hence exhibit additionally an indirect antimicrobial activity. The permeabilizing action of the polymers can increase the uptake of other therapeutically active agents and therefore should be able to potentiate the apparent antimicrobial activity of other drugs and antibiotics.

Medical conditions associated with a pathogenic microorganism include, for example, infections, infestation, contaminations and transmissions by or of pathogenic microorganism. In general, a disease causing infection is the invasion into the tissues of a plant or an animal by pathogenic microorganisms. The invasion of body tissues by parasitic worms and other higher pathogenic organisms is commonly referred to as infestation.

The polymers of the present embodiments can therefore be used in the treatment of medical conditions caused by pathogenic microorganisms by virtue of their anti-microbial effects inflicted upon the pathogenic microorganisms by one of to the abovementioned mechanism, which mostly stem from the pre-determined sequence and composition of the monomer residues comprising the polymer.

The polymers described herein can be further used, like depsipeptides, in the treatment of medical conditions that are associated, for example, with inflammation and/or proliferation, namely, inflammatory diseases or disorders and/or proliferative diseases or disorders.

An exemplary proliferative disease is cancer, including, for example, brain, ovarian, colon, prostate, kidney, bladder, breast, lung, oral and skin cancers, and, more particularly, glioblastoma multiforme, anaplastic astrocytoma, astrocytoma, ependymoma, oligodendroglioma, medulloblastoma, meningioma, sarcoma, hemangioblastoma, pineal parenchymal, adenocarcinoma, melanoma and Kaposi's sarcoma.

Exemplary inflammatory diseases or disorders include, without limitation, perfusion injury of an ischemic organ, e.g., reperfusion injury of the ischemic, myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, diabetes type II, disseminated intravascular coagulation, fatty embolism, Alzheimer's disease, Parkinson's disease, multiple sclerosis, neonate-, infantile- and adult-respiratory diseases, carcinogenesis, hemorrhages in neonates, cerebral vascular disorders and other pathological conditions.

As mentioned hereinabove, in addition to exhibiting a therapeutic activity per se, the polymers described herein can be designed and utilized for attaching thereto various agents.

Depending on the agent to be attached to the polymer, the polymer's properties can be pre-determined so as to allow the formation of the desired interactions between the agent and the polymer. These properties can be determined by virtue of the side chains of the polymer or by virtue of the polymer backbone, namely, its chirality. Thus, for example, for attaching a charged species, polymers characterized by side chains having the opposite charge are prepared. For covalently attaching an agent, polymers bearing appropriate reactive groups are prepared. For attaching an agent via hydrophobic interactions, polymers having hydrophobic side chains are prepared. For attaching a chiral agent, optically active polymers having a complementary stereoselectivity are prepared, as is detailed hereinunder.

Thus, according to still an additional aspect of the present invention there is provided a conjugate comprising a polymer, as described herein, having attached thereto an active agent.

The active agent can be, for example, a therapeutically active agent, a labeling agent, a cross-linking agent or another polymer.

As used herein, the phrase "therapeutically active agent" describes a substance, which exhibits a therapeutic activity when administered to a subject. Representative examples include, without limitation, chemotherapeutic agents, anti-proliferative agents, anti-inflammatory agents, antimicrobial agents, anti-hypertensive agents, statins, psychotropic agents, anti-coagulants, anti-diabetic agents, vasodilating agents, analgesics, hormones, vitamins, metabolites, carbohydrates, peptides, proteins, amino acids, co-enzymes, growth factors, prostaglandins, oligonucleotides, nucleic acids, antisenses, antibodies, antigens, immunoglobulins, cytokines, cardiovascular agents, phospholipids, fatty acids, betacarotenes, nicotine, nicotinamide, anti-histamines and antioxidants.

As used herein, the phrase "labeling agent" refers to a detectable moiety or a probe and includes, for example, chromophores, fluorescent compounds, phosphorescent compounds, heavy metal clusters, and radioactive labeling compounds, as well as any other known detectable moieties. Attachment of labeling agents to polymers described herein can be utilized for diagnostic purposes.

The phrase "cross-linking agent" describes a multifunctional, preferably di-functional, substance that forms chemical interactions, as described herein, with two or more reactive groups and hence can form interactions between reactive groups of two polymers to thereby lead to cross-linking. Representative examples include, without limitation, divalent metal cations such as $Ca^{+2}$, $Mg^{+2}$, $Zn^{+2}$, and the like, which can effect cross-linking between two negatively-charged reactive groups; silicates such as di-, tri- and tetra-orthosilicates, and any other known cross-linking agents.

Attaching a cross-linking agent can be utilized for attaching another polymer to the polymer described herein. However, it should be noted that such an additional polymer can be attached to the polymer described herein via cross-linking that is effected solely by the side groups of the polymers. Thus, for example, cross-linking can be effected between free amine groups in the polymer and free carboxylate groups in the other polymer; and likewise between any other pairs of compatible reactive groups.

Depending on the nature of the active agent, the pre-determined properties of the polymer and the intended use of the conjugate, the active agent can be attached to the polymer via chemical interactions and/or physical interactions.

Chemical interactions include, for example, covalent bonds, electrostatic interactions, hydrogen bonds, hydrophobic interactions, aromatic interactions and stereointeractions. The latter can be beneficially utilized for attaching a chiral therapeutically active agent to the polymer, to thereby form a hetero-stereo complex, as is detailed hereinbelow.

Physical interactions include, for example, encapsulation, namely, by physical absorption or swelling within or on the polymer or entrapment within the polymer.

As used herein, the term "stereointeraction" refers to a combination of non-covalent chemical interactions which occurs between two chiral molecules, such as van-der-Waals interactions, hydrophobic interactions, aromatic interactions, coulombic forces and electrostatic interactions, hydrogen bonds, salt bridges and the likes, which is enhanced and intensified by the specific chiral structure of the interacting species.

Chiral molecules such as peptides, proteins, other macromolecules and small molecules and the polymers presented herein can reach a close-fitting interaction due to their chiral nature and structural "handedness". Such stereointeraction is typical, but not limited to, to two matching stereoisomers, namely enantiomers. For example, in case the active agent is a native peptide, the repetitive backbone structure, having a particular handedness due to the L-amino acids comprising the peptide, can intertwine with a chiral polymer of the present invention, having a particular matching handedness, or twist, and form a hybrid thread, similar to the collagen fiber, as is detailed hereinunder.

Thus, according to an embodiment of this aspect of the present invention, the active agent is a chiral agent, which is attached to the optically active polymer described herein via stereospecific interactions, to thereby form a hetero-stereo complex with the polymer.

Unlike other forms of chemical modifications, complex formation between a chiral agent and a polymer according to the present invention involves a molecular modification of the chiral agent without effecting any chemical alteration of the chiral agent itself. It is a method of modification in which the chemical and/or biological integrity of the agent remains substantially intact. The aforementioned stereointeraction between the polymer presented herein and a chiral agent can exhibit a chirality-driven and structure-specific compatibility, affording a hetero-stereo complex.

Thus, according to another aspect of the present invention there is provided a hetero-stereo complex which includes the optically active polymer presented herein having complexed thereto a chiral agent, wherein the chiral agent has a stereoconfiguration which is suitable for forming a stereointeraction with the polymer.

As used herein, the phrase "hetero-stereo complex", which is also referred to interchangeably as "heterostereoselective complex", refers to a chemical complex between two non-identical, hence hetero, chiral molecules, hence stereo, which are mutually compatible with respect to various chemical moieties thereof which are specifically positioned in space so as to allow close-fitting stereointeraction therebetween, hence selective.

The term "stereoconfiguration" as used herein, refers to the aforementioned spatial configuration or three-dimensional arrangement of chemical moieties within a chiral agent.

According to this aspect of the present invention, the polymer presented herein can be designed so as to specifically match the stereoconfiguration of a chiral agent and thus form a chemical complex based on non-covalent interactions which is selective with respect to other compounds that do not exhibit that specific stereoconfiguration.

Preferably the chiral agent is a chiral therapeutically active agent, such as, but not limited to, peptides, proteins, oligonucleotides, polysaccharides, chiral macromolecules and other small molecules which exhibit chirality and/or handedness such as present in molecular helices.

Exemplary chiral therapeutically active agents include, without limitation, endogenous opioid agonists such as enkephalins and endorphins, hypothalmic hormones such as gonadoliberin, melanostatin, melanoliberin, somatostatin, thyroliberin, substance P, and neurotensin, adenohypophyseal hormones such as corticotropin, lipotropin, melanotropin, lutropin, thyrotropin, prolactin, and somatotropin, neurohypophyseal hormones, calcitropic (thyroid) hormones such as parathyrin and calcitonin, thymic factors such as thymosin, thymopoietin, circulating thymic factor, and thymic humoral factor, pancreatic hormones such insulin, glucagon, and somatostatin, gastrointestinal hormones such as gastrin, cholecystokinin, secretin, gastric inhibitory polypeptide, vasointestinal peptide, and motilin, chorionic (placental) hormones such as choriogonadotropin and choriomammotropin chiral therapeutically active agents, ovarian hormones such as relaxin, vasoactive tissue hormones such angiotensin and brandykinin, growth factors such as somatomedins, epidermal growth factor, urogastrone, and nerve growth factor, hemophilia factors such as blood clotting factors VIII and IX, enzymes such as streptokinase, fibrinolysin, deoxyribonuclease, and asparaginase, and artificial or pseudo peptides such as deferoxamine.

Molecular helices occur frequently in nature, and their specific handed spiral structure effects specific biochemical attributes. The most renowned helix is the double helix of DNA. Peptides of certain amino acid sequences have a tendency to form alpha helices. Another example is the structural motif present in "leucine/valine zipper" proteins. This structural motif is the basis for the configuration of a family of DNA-binding proteins in which leucine/valine residues on two protein alpha-helices interdigitate in zipper fashion to stabilize the protein. This interdigitation is afforded by hydrophobic interactions between leucine/valine residues located at specific intervals along both polypeptide chains that twist one around and along the other to firm a loose double helix; this loose helix has a compatible handedness with respect to the DNA double helix. The triple helix complex of collagen is another example of the effect of the handedness of polypeptide chains. Collagen has a specific amino acid composition and sequence rich in glycine, which is found at almost every third residue, and in praline, as well as two amino acid derivatives, namely hydroxyproline and hydroxylysine, which are formed by enzymatic post-translational modification of proline and lysine at specific locations relative to glycine. Common to all polypeptide (polymer) based helices, is the fact that the handedness thereof is predetermined by the chirality of the amino acids comprising the polypeptide chain.

Like the abovementioned naturally occurring polymer-based and chirality-dependent complexes, the polymers of the present invention can be used to form similar complexes. These complexes can comprise polymers of identical composition, namely homo-complexes, or hybrids of the polymers presented herein and other polymers, such as therapeutically active polymers, namely peptides and proteins.

It is clear from the examples presented hereinabove for the naturally occurring polypeptide complexes, that apart from the handedness of the polypeptide chains, which stems from the chirality of the amino acids, the amino acid sequence is also a key element in the formation and configuration of these complexes. Therefore the side-chains of the chiral pre-polymerized monomers utilized for constructing the polymers of the present invention play a crucial role in the formation and configuration of the aforementioned hetero-stereo complexes. Moreover, the side-chains of the chiral pre-polymerized monomers are the basis for the stereoselectivity of the complex.

For example, in order to form a heterostereoselective complex with a peptide (as the chiral agent) rich in hydrophobic residues, the chiral polymer according to the present invention should present matching hydrophobic side chains which will interact with the hydrophobic residues of the peptide and together with the compatible handedness form a close-fitting heterostereoselective complex therebetween. In an analogous example, the peptide chiral agent can present various hydrogen donor/acceptor side-chain residues and the chiral polymer according to the present invention can present matching acceptor/donor side-chain residues which will interact therebetween in a series of hydrogen bonds.

The hetero-stereo complexes described herein present a novel, highly beneficial, methodology for overcoming the limitations associated with the use of chiral substances such as peptides and proteins as therapeutically active agents.

As a result of the expeditious progress in the fields of biochemistry, molecular genetic engineering and medicine, many biologically active peptides and proteins have been identified as having a great clinical potential as pharmaceuticals. However, the use of peptides and proteins as therapeutically active agent has been limited mainly due to low bioavailability, high chemical sensitivity and instability, namely peptides and proteins are hard to administer enterically, and particularly orally, and have a short shelf-life. To date methods of oral administration of these compounds have not kept pace with their identification and synthesis. The low bioavailability of peptides and proteins stems from the fact that adult animals (including humans) absorb peptides and proteins poorly when these are orally administered due to a combination of factors: destruction of these molecules in the stomach by acid hydrolysis and in the gastrointestinal tract by enzymes capable of cleaving peptide bonds before they can be absorbed, and slow passage of intact these molecules through the intestinal wall because of low lipophilicity. Consequently, therapeutic use of peptides and proteins is limited by the necessity of administering it parenterally, particularly by intravenous or intramuscular injection.

Some non-proteinaceous therapeutically active agents suffer from similar limitations in preparing, handling, storing and administration thereof, due to high chemical instability and low bioavailability as discussed hereinabove.

These limitations associated with preparing biologically active peptides and proteins, and other non-proteinaceous therapeutically active agents, for oral ingestion or other types of enteral administration, can be circumvented by the use of the polymers of the present invention. By forming a hetero-stereo complex with these agents, and by further controlling various properties of the polymer, as is detailed hereinunder, the delivery and release of the chiral active agents complexed to the to polymer is enabled. Thus, the controllable biodegradability and affinity of the polymer, which can be effected as discussed hereinbelow, together with the close-fitting stereointeraction between two chiral entities, namely the therapeutically active agent and the polymer of the present invention, brings about a viable solution to many pharmaceutical hurdles.

When utilized within the conjugates described herein, including the hetero-stereo complexes described herein, the polymer described herein can be designed so as to serve as a highly efficient carrier of therapeutically active agents and/or labeling agents.

The controllability of the polymer's various features, discussed hereinabove, allows the design of such polymers which can serve as finely-controlled carriers for slow-releasing and/or delivering a therapeutically active agent to a targeted bodily site. Acting as such a carrier, the polymer described herein further provides a protecting effect, which enables to administer to a subject otherwise difficult to administer, and/or handle, therapeutically active agents (e.g., proteins).

The protection activity exerted by the polymer of the present invention can stem from physico-chemical characteristics of the polymer, such as its density, crystallinity, and chemical composition. Other characteristics which improves the protection capacity of the polymer may stem from it chirality, such as in the case of a polymer which is composed of D-amino acids and D-amino acids derivatives, which are non-compatible to naturally occurring enzymes, and thus will exhibit a lower rate of decomposition and derogation, as is detailed hereinunder.

Thus, for example, protection of the therapeutically active agent can be provided by the polymer described herein by encapsulating the agent in the polymer. This type of protection allows a highly sensitive therapeutically active agent to pass through the stomach and other parts of the gastrointestinal tract without being digested or otherwise rendered inactive.

To achieve this result, the polymer/therapeutically active agent conjugate must meet the following criteria: (a) it must be resistant to the acidic environment in the stomach; (b) it must be resistant to enzymatic degradation by gastric and pancreatic enzymes; (c) it must be sufficiently lipophilic to pass the intrinsic barrier of the intestinal wall; and finally (d) the changes in physiological and biological properties of the therapeutically active agent resulting from the complexation must be null or minimal so that their therapeutic activity is maintained. While criteria (c) and (d) are basic structural requirements for all enterically administered therapeutically active agents (such as by rectal, buccal or topical routes), criteria (a) and (b) must be met in addition to (c) and (d) for the therapeutically active agent to be orally effective.

The aforementioned criteria (a) and (b) can be met by attaching the therapeutically active agent to the polymer of the present invention.

The chemical protection of the therapeutically active agent is effected by two basic contributions provided by the polymers presented herein: (i) a physical barrier isolating the therapeutically active agent from the digestive environment, namely the acidic environment in the stomach and gastric and pancreatic enzymes, for example by encapsulation of the therapeutically active agent by a thick and/or dense layer comprised of the polymers presented herein; and/or (ii) the chemical composition of the polymer which can comprise backbone bonds which are less susceptible to the acidic environment and/or non-compatible with respect to the digestive enzymes (non-substrate thereof), backbone structure having a non-compatible chirality with respect to the digestive enzymes, and also non-compatible side-chains with respect to the digestive enzymes. Each of these two basic contributions can render the polymer presented herein highly resistant to digestion in the gastrointestinal tract, and hence rendering a therapeutically active agent attached thereto also resistant.

The aforementioned criteria (c) and (d) can also be met by complexing the therapeutically active agent with the polymer of the present invention, so as to form a hetero-stereo complex, as described hereinabove. The complex formed between the therapeutically active agent and the polymer can be made sufficiently lipophilic to pass the intrinsic barrier of the intestinal wall by virtue of the chemical composition of the side-chains of the polymers which can be selected so as to provide this lipophilicity. For example, in cases where the therapeutically active agent is not sufficiently lipophilic, at least some of the side-chains of the chiral pre-polymerized monomers can be selected hydrophobic.

Furthermore, the composition and sequence of the chiral non-polymerized monomers comprising the polymers presented herein can be selected so as to effect an affinity towards specific biologic target such as a somatic organ, tissue or cell type, or an exogenous entity such as a pathogenic microorganism. For example, in cases where the therapeutically active agent is directed at exerting a therapeutic effect in the central nervous system (CNS), at least some of the side-chains of the chiral pre-polymerized monomers can be selected hydrophobic, so as to facilitate permeation through the blood-brain-barrier. Alternatively, in cases where the therapeutically active agent is directed at exerting a therapeutic effect against a pathogenic microorganism, at least some of the side-chains of the chiral pre-polymerized monomers can be selected amphiphatic and/or positively charged.

Similarly, in cases where it is desired that the therapeutically active agent would permeate cells or organ membranes, at least some of the side-chains of the chiral pre-polymerized monomers constructing the polymer are selected positively charged. In addition, the pre-polymerized monomers can be selected so as to form a polymer having a sequence analogous to some known targeted proteins, to thereby achieve affinity of the polymer to the corresponding targets.

Thus, by designing the polymer so as to exhibit the desired protection and/or targeting effect, the conjugates and complexes described herein can be efficiently utilized for delivering a therapeutically active agent to a bodily site.

Thus, according to a further aspect of the present invention, there is provided a method of delivering a therapeutically active agent to a bodily organ of a subject in need thereof. The method is effected by administering to the subject a therapeutically effective amount the polymer presented herein, having the therapeutically active agent attached thereto, as described herein.

The phrase "therapeutically effective amount" or "pharmaceutically effective amount" denotes that dose of an active ingredient or a composition comprising the active ingredient that will provide the therapeutic effect for which the active ingredient is indicated.

The term "delivering" or "delivery" as used in the context of the present invention refers to the act of enabling the transport of a substance to a specific location, and more specifically, to a desired bodily target, whereby the target can be, for example, an organ, a tissue, a cell, and a cellular compartment such as the nucleus, the mitochondria, the cytoplasm, etc.

Similarly, the pre-determined affinity of the polymers described herein can be used for delivering labeling moieties to a targeted site, for diagnostic purposes. This is achieved by administering to a subject in need thereof a diagnostically effective amount of a polymer, as described herein, having attached thereto a labeling moiety, as described herein.

As used herein, the phrase "diagnostically effective amount" denotes that dose of labeling moiety or a composition comprising the labeling moiety that enables to collect the desired data by utilizing the applied diagnostic technique.

The polymers described herein can be further deigned so as to degrade, either biologically (biodegrade) or otherwise chemically or mechanically, selectively at specific environments. This feature can be used to slowly or otherwise controllably release an agent that is attached to the polymer, as described herein.

Hence, according to another aspect of the present invention there is provided a method of slow-releasing an agent to an environment, which is effected by contacting with the environment a conjugate or a heterostereoselective complex which comprises the polymer presented herein having the agent attached thereto, as is detailed herein.

The environment, according to this aspect of the present invention, can be a relatively simple system such as a gaseous environment, a system comprising one or more solvents such as in a reaction mixture, or a complexed system such as a body of an organism, a natural or artificial ecosystem, a natural of artificial habitat, an industrial area, a facility or a device.

In a preferred embodiment, the environment is a body of an organism and the agent is a therapeutically active agent. The polymer described herein is designed to slowly or otherwise controllably release the therapeutically active agent in the body.

Slow release of therapeutically active agents enables to maintain a relatively constant level of the therapeutically active agent in the body and avoids fluctuations of the concentration of the therapeutically active agent within a dosing interval. This enables higher doses to be given less frequently, while maintaining therapeutic concentrations over prolonged periods. Furthermore, slow-release preparations are beneficial in reducing potential side-effects of the therapeutically active agent due to transiently high peak concentrations being reached soon after administration.

The controllable release of an active agent from the conjugates described herein is achieved by controlling the biodegradability of the polymer. Thus, for example, agents that are encapsulated in the polymer or stereocomplexed thereto, are released as a result of the polymer's decomposition. As the polymers slowly degrade/dissolve under a suitable environment (e.g., aqueous, acidic, basic, etc.) and thereby degrade/dissolve in body fluids, the interactions between the polymer and the active agent are reduced and release of the therapeutically active agent(s) is effected.

The rate at which a therapeutically active agent is released is generally dependent on the rate at which the polymer disintegrates or dissolves. Disintegration greatly increases the therapeutically active agent's surface area in contact with GI fluids, thereby promoting agent dissolution and absorption.

Degradation and dissolution rate of the polymer determines the availability of the therapeutically active agent for absorption. When slower than absorption, degradation and dissolution becomes the rate-limiting step. Overall absorption can therefore be controlled by manipulating the chemical composition of the polymer presented herein. For example, using a relatively digestive-resistant polymer may slow down its absorption. This can be achieved by utilizing polymers is which the linkages between the monomer residues are less susceptible to cleavage (e.g., enzymatic or hydrolytic). Such polymers can include, for example, stable linkages such as amide bonds, or, alternatively, be composed of monomer residues deriving from derivatives of D-amino acids, which are stable to enzymatic cleavages, as us detailed hereinabove.

In each of the methods described herein, the polymer, the conjugate or the hetero-stereo complex can be utilized either as is or, preferably, can form a part of a pharmaceutical composition.

Hence, according to another aspect of the present invention, there is provided a pharmaceutical composition which comprises any of the polymers, conjugates or complexes presented herein and a pharmaceutically acceptable carrier.

Also provided is a use of any of the polymers, conjugates and complexes presented herein in the preparation of a medicament.

The pharmaceutical composition and/or the medicaments are preferably identified for use in any of the methods described hereinabove.

As used herein a "pharmaceutical composition" refers to a preparation of one or more of the dendritic compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

The pharmaceutical compositions described herein can be formulated for various routes of administration. Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The compositions may, if desired, be presented in a pack or dispenser device, such as an FDA (the U.S. Food and Drug Administration) approved kit, which may contain the dendritic compound. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

The polymers of the present invention can be further used to form various objects and structures. Structures comprising the chiral polymers of the present invention can be designed suitable for use as a structural element and/or a drug delivery system in many medical procedures and devices. The versatility of the polymer structure enables to design such polymers that would exhibit the desired mechanical, physical, biological and/or chemical properties for the intended use thereof, Hence, according to a further aspect of the present invention there is provided a medical device which comprises a polymer as described herein. Optionally, the medical device comprises a conjugate or a complex, as described herein, in which a therapeutically active agent is attached or complexed to the polymer.

In a preferred embodiment of the present invention, the medical device is a biodegradable device.

Generally, the main motivation to have a biodegradable medical device is to have a device that can be used as an implant and will not require a second surgical intervention for removal. Besides eliminating the need for a second surgery, the to biodegradation may offer the advantage of local, functionally focused drug delivery. For example, a fractured bone that has been fixated with a rigid, non-biodegradable stainless implant has a tendency for refracture upon removal of the implant. Since the stress is borne by the rigid stainless steel, the bone has not been able to carry sufficient load during the healing process. However, an implant prepared from biodegradable chiral polymer as described herein can be engineered to degrade at a rate that will slowly transfer load to the healing bone, while steadily delivering bone-regeneration promoting agent to the locus of the fracture.

In its simplest form, a biodegradable device having a therapeutically active agent delivery capacity consists of a dispersion of the therapeutically active agent, either chiral or non-chiral, in a chiral polymeric coat matrix. The therapeutically active agent is typically released as the biodegradable chiral polymeric coat biodegrades in vivo into soluble products that can be absorbed and/or metabolized and eventually excreted from the body over a period of time which depends on the polymer and the physical dimensions of the device.

In a particularly preferred embodiment, a medical device comprising the polymer described herein is used for implantation, injection, or otherwise placed totally or partially within the body.

In preferred embodiments of the present invention, the medical device is adapted for transdermal and/or topical applications in a subject. It is particularly important that such medical device would cause minimal tissue irritation when used to treat a given tissue.

Exemplary devices which can be used for transdermal application include, without limitation, a suture, an adhesive plaster and a skin patch.

Exemplary devices which can be used for topical application include, without limitation, a suture, an adhesive strip, a bandage, an adhesive plaster, a wound dressing and a skin patch.

In more preferred embodiments, the medical device of the invention is adapted for implanting the medical device in a bodily organ of a subject. It is particularly important that such medical device, other than serving its intended purpose, would not evoke an immune response resulting in systemic failure upon rejection which may be detrimental and even fatal.

Exemplary devices which can be used for implanting in a bodily organ of a subject include, without limitation, a plate, a mesh, a screw, a pin, a tack, a rod, a suture anchor, an anastomosis clip or plug, a dental implant or device, an aortic aneurysm graft device, an atrioventricular shunt, a catheter, a heart valve, a hemodialysis catheter, a bone-fracture healing device, a bone replacement device, a joint replacement device, a tissue regeneration device, a hemodialysis graft, an indwelling arterial catheter, an indwelling venous catheter, a needle, a pacemaker, a pacemaker lead, a patent foramen ovale septal closure device, a vascular stent, a tracheal stent, an esophageal stent, a urethral stent, a rectal stent, a stent graft, a suture, a synthetic vascular graft, a thread, a tube, a vascular aneurysm occluder, a vascular clip, a vascular prosthetic filter, a vascular sheath and a drug delivery port, a venous valve and a wire.

Examples of bodily sites where a medical device of the present invention may be used include, without limitation, skin, scalp, a dermal layer, an eye, an ear, a small intestines tissue, a large intestines tissue, a kidney, a pancreas, a liver, a digestive tract tissue or cavity, a respiratory tract tissue or cavity, a bone, a joint, a bone marrow tissue, a brain tissue or cavity, a mucosal membrane, a nasal membrane, the blood system, a blood vessel, a muscle, a pulmonary tissue or cavity, an abdominal tissue or cavity, an artery, a vein, a capillary, a heart, a heart cavity, a male reproductive organ, a female reproductive organ and a visceral organ.

Preferred medical devices according to the present invention include stents, wound dressings, sutures and suture anchors, interference and general screws, angioplastic plugs, pins and rods, tacks, plates, meshes, anastomosis clips and rings, dental implants and guided tissue matrixes.

In a world where environmental conservation becomes critical, biodegradable products which are not necessarily for medical purposes and uses are of great importance and need. Many disposable products are turned environmentally-friendly by using biodegradable compounds in their production. As known in the art, there are many such products and raw materials available, yet the use of the polymers of the present invention to produce disposable goods and products has an added benefit stemming from the presence of other beneficial agents therein, preferably chiral agents.

Thus, according to preferred embodiments of the present invention the polymers, conjugates and complexes presented herein can be used in the construction of various articles-of-manufacture. Such articles-of-manufacture may include, without limitation, fishing lines and nets, insect and bird nets, vegetation nets, woven and non-woven cloths and fibers, disposable women's sanitary items, disposable facial masks (as used by surgeons), wet "paper" tissues (wipes), disposable underwear, disposable handkerchiefs, towels and diapers, disposable medical supplies, disposable food containers or dishes, disposable items of clothing, disposable cutlery items and other disposable consumer and industrial products.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Methods

All reagents, solvents and starting materials were purchased from known vendors such as Sigma-Aldrich, Fluka and Merck, Acros, Novabiochem, Calbiochem, GeneScript, Iris Biotech, and GL Biochem (Shanghai), unless otherwise indicated.

Amino acids were purchased from Sigma-Aldrich, and from Shijiazhuang shixing amino acid Co., Ltd. China.

Characterization of the physical properties of the polymers is conducted by circular dichroism spectroscopy, differential scanning calorimetry (DSC), NMR measurements, high resolution scanning electron Microscopy (HR-SEM), cryogenic transmission electron microscopy (Cryo-TEM), small angle Xray Scattering (SAX), and molecular weight determination.

Circular Dichroism Spectroscopy: Circular Dichroism Spectroscopy (CD) measurements are carried out at 20° C. on a JASCO J-720 spectrometer. The ellipticity is calibrated with (+)-10-camphorsulfonic acid. Spectra are recorded in the range of 180-340 nm at a speed of 50 nm/minute with a resolution of 0.2 nm. The mean residue molar ellipticity [θ] MRW is calculated using the formula:

$$[\theta]MRW = \theta/10 Cr \times L$$

Cr being the mean residue molar concentration, and equaling n×Cp n being the number of peptide bonds, and Cp being the molar concentration in moles per liter, L being the path length in centimeters, and θ is the ellipticity in millidegrees.

Quantitative analysis of the secondary structure is achieved by fitting the CD data with CDFasman algorithm. Measurements are carried out in water (in case of soluble polymer) and in various concentration of Tetrafluoroethylene (TFE).

Differential scanning calorimetry (DSC): Thermal analysis is carried out using a TA instrument MDSC 2910 t calibrated with indium. After loading a sample (about 9 mg) into the DSC, the temperature is brought to 0° C. and maintained at that temperature for 1 minute. The thermograms are recorded at a heating rate of 10° C./minute. The melting temperature, Tm, is determined from the maximum in the melting endotherm. The heat of melting, delta H, is determined by the peak area of the melting endotherm.

NMR measurements: $^1$H-NMR analyses were performed on a Varian 300 MHz spectrometer.

Mass Spectroscopy: Mass Spectroscopy (MS) was performed using a Finigen LCQ mass spectrophotometer.

Infrared Spectroscopy Infrared Spectroscopy (IR) measurements were carried out using an Anelect Instruments FT-IR model fx-6160 on samples cast on NaCl plates from solutions in $CH_2Cl_2$ instrument. IR spectra were recorded between 1000 and 4000 $cm^{+1}$.

High Resolution Scanning Electron Microscopy (HR-SEM): The surface morphologies of the polymers is examined by high resolution scanning electron microscopy (HR-SEM) using a sirion scanning microscope (FEI Company, Holand) equipped with a Shottky type field emission source at 30 kV accelerating voltage. Particles are deposited on a carbon film followed by gold coating in vacuum for one minute at 20 mA.

Cryogenic Transmission Electron Microscopy (Cryo-TEM): Vitrified specimen for direct imaging cryo-TEM is prepared in a controlled environment virtification System (CEVS). Specimen in solution is applied to a perforated carbon film used as specimen support with hole of one micron in diameter. The specimen is examined in the microscope operated at 120 kV. Images are recorded digitally in minimal electron dose by CCD camera.

Small Angle Xray Scattering (SAX): SAX measurements are carried out using slit collimated incident beam (Kratky camera, A. Paar Co.), Ni-filtered CuK radiation. Scattering in the direction perpendicular to the slit-length direction of the incident beam is recorded with a linear position-sensitive detector (Raytech) coupled to multichannel analyzer (Nucleus). The sample to detector distance is 260 mm.

Molecular weight determination: Molecular Weight (Mn and Mw) and polydispersity (PD) are determined by gel permeation chromatography (GPC) using a Waters liquid chromatograph equipped with a 410 differential refractometer (RI detector). N,N'-dimethyl formamide (DMF) containing 0.01% lithium bromide is used as an eluent at a flow rate of 1.0 ml/minute. A styragel column of pore sizes 103±106 Å is used. The molecular weight calibration is carried out using polystyrene standards having molecular weight (MW) in the range $2.9 \times 10^3$ to $1.7 \times 10^5$ grams/mol.

Example 1

Preparation of α-hydroxy acids from α-amino acids by diazotization

α-Amino acids were converted into the corresponding hydroxyl carboxylic acids using sodium nitrate in sulfuric acid (according to the procedure described in Bauer and Gajewiak [Tetrahedron 60 (2004) 9163-170], or in a AcOH/H$_2$O solution (according to the procedure described by Songpon Deechongkit et al. [*Org. Lett.*, 6, p. 497-500, 2004], as depicted in Scheme 1 below:

Scheme 1

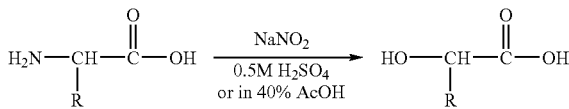

whereas:
R=CH$_3$, (CH$_3$)$_2$CH, (CH$_3$)$_2$CHCH$_2$, CH$_3$CH$_2$(CH$_3$)CH, CH$_3$SCH$_2$CH$_2$, C$_6$H$_5$CH$_2$, HOCH$_2$, CH$_3$CH(OH), HSCH$_2$, H$_2$NCOCH$_2$, H$_2$NCOCH$_2$CH$_2$, HOOCCH$_2$, HOOCCH$_2$CH$_2$, NH$_2$(CH$_2$)$_4$, H$_2$NCNHNH(CH$_2$)$_3$, C$_3$N$_2$CH$_2$ (Histidine side chain)

The α-amino acids were treated at 0° C. with an excess of aqueous sodium nitrate in the presence of 0.5 M sulfuric acid. The reaction mixture was stirred overnight at room temperature, and after work-up, the resulting α-hydroxy acids were crystallized from organic solvents.

In a typical synthesis, amino acid (10 mmol) was dissolved in H$_2$SO$_4$ (40 ml of a 0.5 M solution, 20 mmol) or in 40% acetic acid (AcOH, 40 ml, 20 mmol). The solution was cooled to 0° C. and a solution of NaNO$_3$ (4.14 grams, 60 mmol) in H$_2$O (13.5 ml) was slowly added while stirring and maintaining the temperature lower than 5° C. The obtained mixture was stirred at this temperature for additional 3 hours. The mixture was then allowed to warm up to room temperature and was left for 24 hours. Then, the mixture was saturated with sodium chloride and was extracted 3 times with ethyl ether (3 aliquots of 50 ml), and the combined organic layer was washed with brine (50 ml) and dried over anhydrous sodium sulfate or magnesium sulfate. The drying agent was filtered off, and ether was evaporated under reduced pressure. The residue was recrystallized from a hexane:ether solution to give the respective α-hydroxy acid.

Using the procedure above, α-hydroxy carboxylic acids were prepared, generally on a 0.1 mol scale, from the following D- or L-amino acids: leucine, isoleucine, valine, phenylalanine, serine and threonine. The α-hydroxy carboxylic acids of serine and threonine were transformed to the O-benzyl ether thereof, as indicated below (see, Compounds 11 and 12). A large-scale procedure for preparing α-hydroxy carboxylic acids is described in Example 2 below. The preparation of α-hydroxy carboxylic acids from tyrosine and tryptophan is described in Example 3 hereinbelow.

(S)-2-Hydroxy-3-phenylpropanoic acid (Compound 1): colorless needles with characteristic pleasant smell; yield 65% (1.08 grams, 6.2 mmol).

Melting Point (Mp): 123-123° C. (compared to the literature 123-124° C.).

$[\alpha]_D^{20}=-21.3$, c=2.35, H$_2$O (compared to the literature $[\alpha]_D=-20.0$, c=2, H$_2$O).

(S)-2-Hydroxy-3-methylbutanoic acid (Compound 2): colorless needles with intensive unpleasant smell; yield 65%.

Mp: 61-62° C. (compared to the literature 62-63° C.).

$[\alpha]_D^{20}=+17.3$, c=1.06, CHCl$_3$ (compared to the literature $[\alpha]_D=+17.3$, c=1, CHCl$_3$);

$[\alpha]$(c=1.58, MeOH): +4.4.

$^1$H-NMR: 3.71 (1H, d), 1.88 (1H, m), 0.86 (3H, d), 0.78 (3H, d).

Analysis: C, 50.68; H, 8.67.

(S)-2-Hydroxy-4-methylpentanoic acid (Compound 3): colorless needles; yield: 65%.

Mp: 78° C. (compared to the literature 78-80° C.).

$[\alpha]_D^{20}=-26.6$, c=1.2, 1 M NaOH (compared to the literature $[\alpha]_D=-25.9$, c=1, 1M NaOH).

$[\alpha]$(c=1.67, MeOH): -9.6.

$^1$H-NMR: 3.91 (1H, dt), 1.73 (1H, m), 1.40 (2H, m), 0.86 (6H, dd); Analysis: C, 54.55; H, 9.30.

(2S,3S)-2-Hydroxy-3-methylpentanoic acid (Compound 4): colorless needles; yield 60%.

Mp: 51° C. (compared to the literature 52-54° C.

$[\alpha]_D^{20}=+21.9$, c=1, CHCl$_3$) (compared to the literature $[\alpha]_D^{22}=+22$, c=1, CHCl$_3$); $[\alpha]$(c=1.31, MeOH): +8.2.

$^1$H-NMR: 3.75 (1H, d), 1.65 (1H, m), 1.38 (1H, m), 1.12 (1H, m), 0.84 (3H, d), 0.81 (3H, t)

(S)-2-Hydroxyhexanoic acid (Compound 5): white crystals; yield 30% (0.40 grams, 3.0 mmol).

Mp: 59-60° C. (compared to the literature 60-61° C.).

$[\alpha]_D^{20}=-16.3$, c=3.92, 1M NaOH (compared to the literature $[\alpha]_D^{25}=-15.3$, c=1.1, 1M NaOH).

(S)-2-Hydroxy-3,3-dimethylbutanoic acid (Compound 6): small colorless crystals; yield 47% (0.62 grams, 4.7 mmol).

Mp: 47-48° C. (compared to the literature 49-51° C.).

$[\alpha]_D^{22}=+4.1$, c=1.83, H$_2$O (compared to the literature $[\alpha]_D^{25}=+4.5$, c=1, H$_2$O).

(S)-2-hydroxy-3-phenylpropionic acid (Compound 7): yield 65%

Mp: 123° C.

$^1$H-NMR: 7.23 (5H, m), 4.14 (1H, dt), 2.87 (2H, dq).

$[\alpha]$(c=1.50, MeOH): -16.1.

Analysis: Found, C, 64.79; H, 6.20; Calculated, C, 65.05; H, 6.07

(R)-2-hydroxy-3-phenylpropionic acid (Compound 8): yield 65%

Mp: 123° C.

$^1$H-NMR: 7.23 (5H, m), 4.12 (1H, dt), 2.85 (2H, dq).

EA: C, 64.80; H, 6.25;

$[\alpha]$(c=1.66, MeOH): +17.8.

(R)-2-hydroxy-4-methylpentanoic acid (Compound 9):
Yield: 65%.

$^1$H-NMR: 3.89 (1H, dt), 3.33 (OH, bp), 1.70 (1H, m), 1.38 (2H, m), 0.84 (6H, dd);

Mp: 78° C.

$[\alpha]$(c=1.61, MeOH): +11.8.

(R)-2-hydroxy-3-methylbutanoic acid (Compound 10):
Yield: 55%.

$^1$H-NMR: 3.71 (1H, d), 1.89 (1H, m), 0.87 (3H, d), 0.80 (3H, d);

Mp: 61° C.

$[\alpha]$(c=1.68, MeOH): -2.7;

Analysis: Found, C, 50.60; H, 8.49; Calcd. C, 50.84, H, 8.53.

(S)-3-Benzyloxy-2-hydroxy-butyric acid (Compound 11): $^1$H-NMR: 6.92 (5H, m), 4.34 (2H, s) 3.99 (1H, dq), 3.74 (1H, d), 1.18 (3H, d);

Analysis: C, 62.85; H, 6.71 (Calculated: 62.32; H, 6.41).

(S)-3-Benzyloxy-2-hydroxy-Propionic acid (Compound 12):

$^1$H-NMR: 7.31 (5H, m), 4.62 (2H, d) 4.12 (1H, m), 3.82 (2H, dd);

Analysis: C, 60.72; H, 5.85 (Calculated: 61.22; H, 6.16).

Example 2

Large Scale Preparation of α-Hydroxy Acids from α-Amino Acids by Diazotization

The same general outline depicted in Scheme 1 above, is used to prepare larger amounts of α-hydroxy acids, with slight modifications.

In an exemplary experiment, (S)-hydroxyisovaleric acid was prepared by equipping a 1 liter, three-necked, round-bottom flask with an overhead stirrer, pressure-equalizing addition funnel, and a thermometer. The flask was charged with L-(+)-isovaline (71.0 grams, 0.61 mol) and water (0.3 liter) was added, affording a white suspension. Concentrated sulfuric acid (31.4 grams, 0.32 mol) was slowly added while stirring, affording a clear solution. Ice (0.2 kg) was then added and the reaction mixture was cooled to below 5° C. A solution of sodium nitrite (53.0 grams, 0.62 mol) in water (0.2 liter) was thereafter slowly added, while maintaining the reaction temperature lower than 5° C., using an ice-water bath. Once the addition of sodium nitrite was completed, the stirred mixture was allowed to slowly warm to ambient temperature (overnight). The pH of the reaction mixture was adjusted to 3-4 by slowly adding solid sodium bicarbonate, and the resulting mixture was extracted with ethyl acetate (3 aliquots of 200 ml). The combined organic extracts were dried over magnesium sulfate, clarified, and concentrated. The residue was recrystallized from a 3:1 mixture of ethyl acetate:hexanes to afford f the corresponding hydroxyl acid as a white solid (Compound 13, 60% yield).

$[\alpha]_D^{20}$=+13.5° (c 1, CHCl$_3$);

IR (KBr): 3425, 2971 and 1711 cm$^{-1}$;

$^1$H NMR (300 MHz, CDCl$_3$): δ=4.16 (d, 1H, J=3.5 Hz), 2.17 (m, 1H), 1.07 (d, 3H, J=6.7 Hz), and 0.93 (d, 3H, J=7.0 Hz) ppm.

Example 3

Preparation of α-Hydroxy Carboxylic Acids of L-Trp and L-Tyr by Diazotization (+) L-Tryptophan (L-Trp) and L-Tyrosine (L-Tyr) hydroxy acids were prepared by first protecting the amino acid by a relevant protecting group.

Preparation of (S)-2-hydroxy-3-(1H-indol-3-yl)pro-pionic acid

Compound 14

Boc-Trp(For)-OH was dissolved in a solution of 80% trifluoroacetic acid (TFA) in dichloromethane (DCM) and the mixture was stirred for 2 hours. The solvent was thereafter evaporated under reduced pressure and the TFA salt of Trp (For)-OH was precipitated in ether. The precipitate was filtered, dried and treated to yield the respective hydroxy acid as described in Example 1 hereinabove. The obtained oily reddish product was then purified on preparative HPLC to obtain (S)-2-hydroxy-3-(1H-indol-3-yl)propionic acid (Compound 14).

$^1$H-NMR: 8.71 (1H, lq), 7.59 (2H, t), 7.32 (3H, q), 4.26 (1H, t), 2.98 (2H, dq).

Preparation of L-Tyr Hydroxy Acid

Compound 15

The phenol residue of tyrosine (Tyr) was first protected, by a benzyl(Bzl) group. Thus, L-Tyr (0.1 mol) was dissolved in 2N NaOH (2 equivalents), and a solution of CuSO$_4$ (0.5 equivalents) in water (50 ml) was added. After heating the mixture to 60° C. and cooling, methanol (350 ml) and 2N NaOH (15 ml) were added. To the resulting mixture benzyl bromide was added (1 equivalent) and the mixture is stirred overnight at 25-30° C. The purple precipitate was thereafter filtered, washed with a mixture of methanol-water, then with methanol and dried. The copper complex was triturated and washed on a sinter glass with 1N HCl (5 aliquots of 50 ml), water (2 aliquots of 25 ml), 1.5N NH$_4$OH (5 aliquots of 25 ml) and finally with water (2 aliquots of 25 ml).

The thus obtained protected L-Tyr was then treated with sodium nitrite in 20% acetic acid, according to the procedure described Deechongkit et al. [Organic Letters, 6, 4, 497-500, 2004], to obtain L-Tyr hydroxy acid (Compound 15).

Yield: 63%;

Mp: 260° C.;

ESI-MS. Found: 272.52, calculated MH$^+$: 272.3.

Example 4

Preparation of α-Hydroxy-Carboxylic Acids Using a Coupled Enzyme System

The deaminase reaction is carried out via whole-cell-biotransformation, as depicted in Scheme 2 below:

Scheme 2

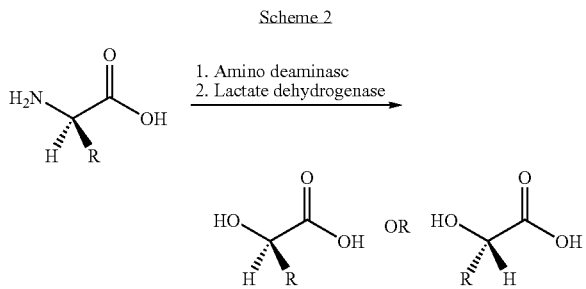

E. coli (100 grams, wet cell pellet), which is carrying a multi-copy clone of the gene for L-amino acid deaminase, was added to deionized water (500 ml) containing L-phenylalanine (100 mmol). The reaction was mixed rapidly in a 2 liter closed fermentor at 32° C., pH 7.5-8, with oxygen sparged into the system at a rate of 1 v.v.m. Deamination was allowed to continue until dissolved oxygen started to rise (approximately after 1 hour) at which point oxygen flow was shut off. The dehydrogenation reaction was initiated by adding a solution containing sodium formate (500 ml, 100 mmol), mercaptoethanol (1 mmol), dithiothreitol (1 mmol), Tris-Cl (25 mmol), nicotinamide adenine dinucleotide (1 mmol), D-lactate dehydrogenase (from S. epidernzidis, 3,800 units) and formate dehydrogenase (from C. boidinii, 380 units). The reaction was carried out at room temperature with nitrogen sparged at 0.05 v.v.m., and while maintaining the reaction pH at 7.5 with 1 N HCl. After 32 hours the titer of D-PLA (D-phenyl lactic acid) was 9.24 grams/liter, corresponding to a 58.1% yield with respect to L-phenylalanine.

Example 5

Preparation of Chiral Ethylene Glycol and Aminoethanol Building Blocks

Chiral α-ethylene glycol (hAAh) derivatives of hydroxy amino acids, prepared according to any of Examples 1-4 above, were prepared by reduction of the carboxylic group to the corresponding alcohol, using a NaBH$_4$/I$_2$ system, as depicted in Scheme 3 below:

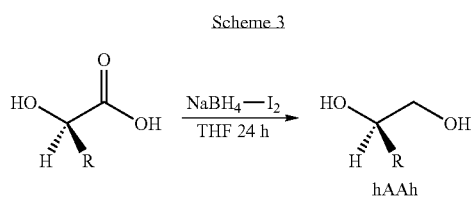

Preparation of chiral 2-alkyl-1,2-diol amino acid derivatives:

Protection of the α-hydroxy group: α-Hydroxy acid is reacted with dihydropyran (1.4 equivalents) and p-toluene sulfonic acid ((PTSA) 0.02 equivalents) in CHCl$_3$, at room temperature, for one hour, affording the corresponding THP-protected acid in 80% yield.

Preparation of chiral 2-alkyl-1,2-diol: A 100 ml of round bottom flask is charged with sodium borohydride (40 mmol) and THF (40 m). A THP-protected hydroxy acid (20 mmol) is added in one portion, the flask was flushed by Argon, and the mixture is cooled to 0° C. in an ice bath. A solution of iodine (16 mmol) dissolved in THF (10 ml) was slowly added, dropwise, during 30 minutes, and a vigorous evolution of hydrogen is observed. Once the addition of iodine is completed and gas evolution is ceased, the mixture is heated to reflux for 18 hours. Upon cooling to room temperature, methanol is added cautiously until the mixture becomes clear. After stirring 30 minutes, the solvent is evaporated and the residual white paste is dissolved in 20% aqueous solution of KOH (50 ml). The solution is stirred for 4 hours and is thereafter extracted with methylene chloride (3 aliquots of 50 ml). The combined organic extracts are dried over sodium sulfate, and concentrated under reduced pressure, affording a white semisolid which is purified by chromatography on silica column. The product is obtained in 80% yield.

Preparation of Chiral Amino Ethanols:

Chiral amino ethanol derivatives of amino acids (nAAh) were prepared from the corresponding amino acids by reduction using NaBH$_4$ and I$_2$, according to the procedure described above, as depicted in Scheme 4 below:

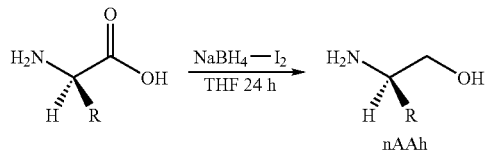

Example 6

Synthesis of Polyesters by Direct Condensation of α-Hydroxy Acids

The polymerization of the α-hydroxy acids, prepared as described in Examples 1-4 hereinabove, was carried out by direct condensation, using three alternative routes (a, b, c), as depicted in Scheme 5 below:

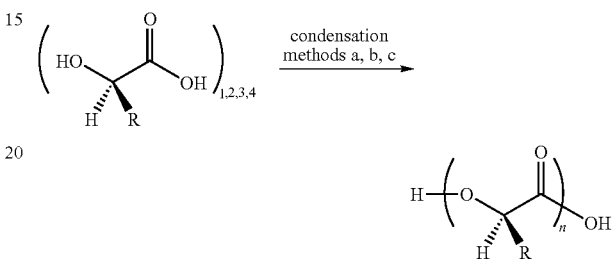

Exemplary condensation reactions were performed with (S)-2-hydroxy-3-methylbutanoic acid (Compound 2, derived from L-Valine).

Method A (Bulk polymerization): α-Hydroxy acid (300 mg) and PTSA (3 mg) were dried overnight by azeotropic distillation in 6 ml toluene (by reflux in a Dean-Starck apparatus). The solvent was thereafter removed under reduced pressure and the reaction mixture was heated at 110° C. for additional 3 hours under vacuum, to obtain a polyester having a molecular weight higher than 4000 Da.

Method B (Solution polymerization, water exclusion): α-Hydroxy acid (300 mg) and PTSA (3 mg) were dried overnight in a Dean-Starck apparatus, as described hereinabove. After 18 hours, the toluene was partially removed. The remaining reaction mixture, containing 1-2 ml toluene, was further heated at about 140° C. for additional 8 hours under reduced pressure (15 mmHg), to obtain a polyester having a molecular weight higher than 5000 Da.

Method C (Acyl Chloride): An α-hydroxy acid was converted to the acyl chloride thereof, using known procedures. The obtained acyl chloride, in dry hot toluene was then reacted with the α-hydroxy acid, so as to form an ester bond, liberating hydrochloride acid during the reaction.

Method D (microwave technique): α-Hydroxy acid (300 mg) and PTSA (3 mg) are dissolved in dry toluene and the mixture is allowed to react in a microwave compartment at high temperature, while azeotropically distilling out the formed water.

Example 7

Synthesis of Polyesters by Ring Opening Via a Lactone Intermediate

Ring opening polymerization of the α-Hydroxy acids described herein was conducted as depicted in Scheme 6 below:

Scheme 6

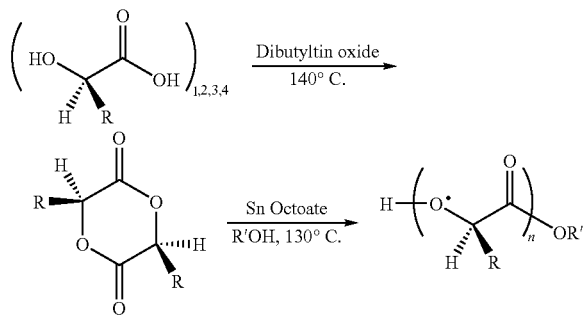

Preparation of a Lactone Intermediate:

Generally, a lactone derivative is first prepared by reacting any one of the α-hydroxy acids, prepared as described in Examples 1-4 hereinabove, with dibutyltin oxide as catalyst, and 2-[2-Methoxyethyloxy]ethanol or 2-[2-Methoxyethyloxy]decanol (1-3 weight percents) as initiators at 140° C. Lactone formation can optionally be prepared without the addition of catalysts.

In an exemplary procedure, 2-hydroxy-3-methylbutanoic acid (Compound 2) was dried by heating in toluene using a Dean-Starck apparatus for 12 hours. Dibutyl tin as catalyst was added and the toluene was then evaporated. The reaction vial was heated to 70° C. under high vacuum (oil pump) for 10-12 hours, to obtain the 3,6-diisopropyl-1,4-dioxane-2,5-dione lactone (Compound 16), as depicted in Scheme 7 below.

Scheme 7

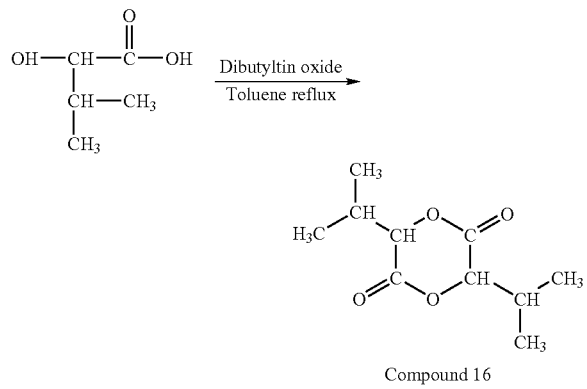

Compound 16

$^1$H-NMR: δ=4.70 (1H-ester, d), 2.49 (1H, ds), 1.15 (3H, d), 1.06 (3H, d).

IR: ν=1749 cm$^{-1}$ (ester);

Mp: 124° C.

The same process was repeated, starting from lactic acid, and resulting in white crystals. The crystals were sublimated, and characterized by NMR, IR and Mp (data not shown).

Ring opening polymerization (ROP) of the lactone intermediate:

The obtained lactones are then polymerized in the presence of a catalyst, either is solution or in the bulk, as follows. Exemplary catalysts include Sn(Oct)$_2$, Yttrium isopropoxide, and (2,4-Di-tert-butyl-6-{[(2'-dimethylaminoethyl)methylamino]methyl}phenol) ZnEt.

Solution ROP Polymerization: In a typical experiment, to a 50 ml round-bottomed flask, equipped with dean-stark apparatus, reflux condenser and CaCl$_2$ tube, isopropyl-hydroxy acetic acid lactone (Compound 16, 600 mg), prepared as described above, and 10 ml toluene are added. The lactone is dried by gradually evaporating out about 9 ml of the toluene during 4 hours, Sn(Oct)$_2$ (10 mg) is thereafter added and the mixture is heated at 135° C. Monitoring the reaction progress is performed by molecular weight determination of removed samples. After 24 hours, the mixture is cooled and the final molecular weight of the product is determined.

Bulk ROP Polymerization: A lactone intermediate, prepared as described hereinabove (600 mg), is degassed for two hours with dry nitrogen at 150° C., Sn(Oct)$_2$ (10 mg) is added, and the mixture is heated to 135° C.

Alternatively, polymerization is conducted using standard high vacuum technique (in sealed glass ampoules), at 80° C. for 10 hours.

Further alternatively, the lactone intermediate (2000 mg) is dried by azeotrop distillation with toluene. Yttrium isopropoxide (100 mg) is added to the dried lactone and the mixture is heated at 120° C. for 24 hours.

In each of the above procedures, polymers having a molecular weight higher 10,000 Da are obtained. The lactone intermediates can be prepared either from a single α-hydroxy acid (e.g., Compound 2 or lactic acid), or from a mixture thereof.

Example 8

Synthesis of Polyesters Via Reaction with Ketones

A promising method for alpha polyester formation takes the advantage of the bidentate nature of the hydroxy acid, which can be readily protected and/or activated.

This method is based on a one-step synthesis that involves heterocyclization of the α-functionality of the hydroxy acid the carboxylic group upon reaction with a ketone or an aldehyde. The obtained lactone includes an activated carboxylic group, which upon a nucleophilic attack by alkoxide in converted to the corresponding 1-carboxy ester. Concomitantly the α-hydroxy function is deblocked. The reaction course is depicted in Scheme 8 below:

Scheme 8

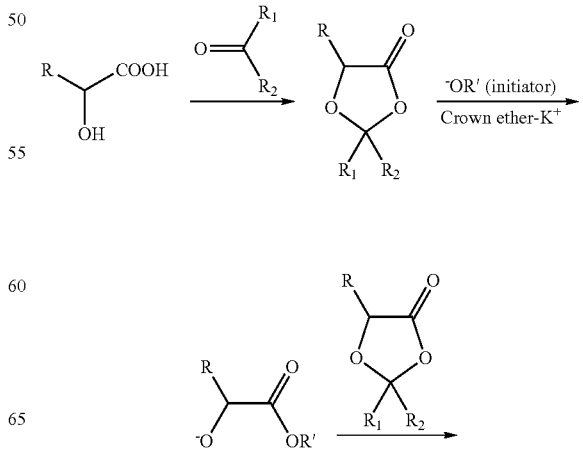

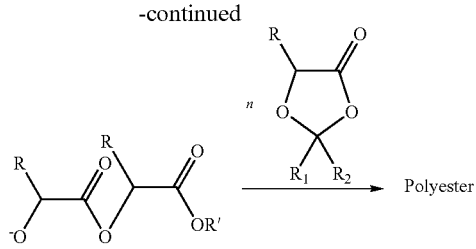

R is as described hereinabove, $R_1$ and $R_2$ are each $CF_3, CH_3$ or together form cyclohexyl Preparation of an Activated Lactone:

α-Hydroxy acids are reacted with ketones to obtain an activated lactone, as depicted in scheme 9 below:

Scheme 9

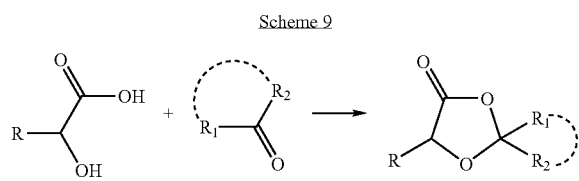

R is as described hereinabove, $R_1$ and $R_2$ are each $CF_3, CH_3$ or together form cyclohexyl Thus, 1,3-oxazolidine-5-ones were prepared according to Böttcher et al. [Monatshefte für Chemie 135, 1225-1242 (2004)].

Preparation of 2,2-[bis-(trifluoromethyl)]-1,3-oxazolidine-5-one: α-Hydroxyester (300-400 mg) was added to toluene (5 ml), hexafluoroacetone (6 equivalents) was then added and the mixture was stirred for 3 hours. Thereafter the mixture was concentrated under reduced pressure and the residue was subjected to polymerization without further purification Preparation of 2,2-[cyclohexyl]-1,3-oxazolidine-5-one: α-Hydroxyester (300-400 mg) was added to toluene (10 ml), cyclohexanone (1 ml) was then added and the mixture was refluxed for 16 hours with a Dean-Starck apparatus. Thereafter the mixture was concentrated under reduced pressure and the residue was subjected to polymerization without further purification.

Preparation of 2,2-dimethyl-1,3-oxazolidine-5-one: α-Hydroxy acid and p-toluene sulfonic acid (PTSA, 1%) were refluxed in acetone for a week, while monitoring the reaction progress by TLC. The acetone was thereafter removed under reduced pressure and the obtained product was characterized by NMR and subjected to polymerization.

Polymerization of the activated lactone:

A substituted 1,3-dioxolan-ones, prepared as described hereinabove, was dissolved in toluene, sodium propoxide (in crown ether, 1 weight percent) was then added and the mixture was refluxed for 24 hours. The solvents were thereafter removed under reduced pressure to afford the corresponding polyester (MW higher than 5,000 Da).

Example 9

Enzymatic Synthesis of Polyesters

A α-hydroxy acids, prepared as described in Examples 1-4 hereinabove, is converted to the corresponding ester, and is then reacted with a lipase in a non-aqueous solution (e.g., hexane), as depicted in Scheme 10 below:

Scheme 10

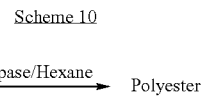

Example 10

Chiral Polyesters Containing α-Hydroxy Acids Building Clock

Using the various building blocks described hereinabove and the various polymerization routes, various chiral polyesters are prepared. These polymers can be divided into four categories according to the chemical features of their building blocks used, as is depicted in FIG. 1.

Category A presents polyesters derived from either a single α-hydroxy acid (hAA) unit (a uniform polymer, denoted as 1A in FIG. 1) or from building blocks composed of 2, 3 or 4 conjugated hydroxy acids having varying side chains (denoted as 2A, 3A and 4A, respectively, in FIG. 1).

Category B presents polyesters originated from a mixture of an α-hydroxy acid unit and any aliphatic or aromatic hydroxy acid. An exemplary polyester in this category is HO-Peg-COOH.

Category C presents polyesters originated from a mixture of a substituted chiral ethylene glycol (or glycerol) unit linked to any dicarboxylic acid (DA).

Category D presents intrinsic compounds related to category C, which are composed of chiral ethylene glycol (hAAh) unit and a chiral dicarboxylic acid unit derived from aspartic or glutamic acid.

The building block units utilized for preparing the polyesters in each of the above categories are prepared as follows:

Preparation of Building Blocks of Category A:

Category A building blocks (1A, 2A, 3A, 4A, FIG. 1) are prepared according to Kuisle et al. [Tetrahedron Letters 40 (1999) 1203-1206]. Briefly, the α-hydroxyl group of the hydroxy acid (hAA) is protected by means of a tetrahydropyranyl (THP) ether group and is subjected to solid support synthesis using either Wang resin or trityl resin (100 micromole). Coupling of hydroxy acid residues is performed using diisopropylcarbodiimide (DIC) (3 equivalents), Dimethylamino pyridine(DMAP) (1 equivalent), and THP-protected hydroxy acid (3 equivalents) for 2 hours. Removal of the THP protecting group in each step is performed by reacting the formed conjugate with PTSA (5 mg/ml) in a $CH_2Cl_2$:MeOH (97:3) mixture, at room temperature for 2 hours. The obtained building block is then cleaved from the resin using a 1:1 $TFA:CH_2Cl_2$ solution (1 hour at room temperature).

Preparation of Building Blocks of Category B:

The preparation of a representative building block of Category B (1B, FIG. 1) is depicted in Scheme 11 below.

Scheme 11

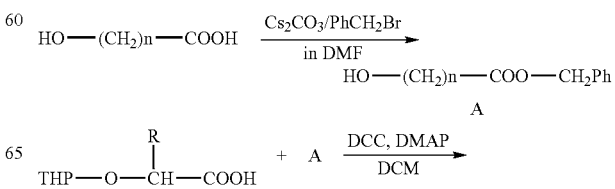

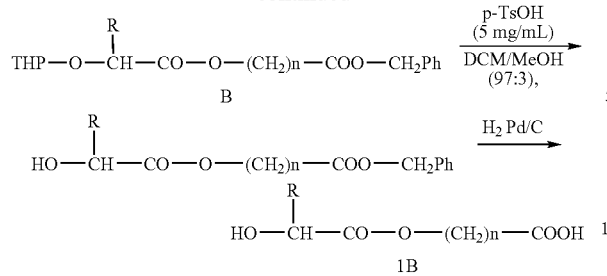

First, the carboxylic group of any of the hydroxy acids utilized, is protected by reacting the hydroxy acid (1 equivalent) with benzyl bromide (1 equivalent) in the presence of cesium carbonate (1.2 equivalents) in DMF, to afford Compound A (Scheme 11). Compound A is then coupled to a THP-protected α-hydroxyl acid in the presence of DCC and DMAP. The organic phase is washed with $Na_2HCO_3$, dried over $MgSO_4$ and evaporated to afford compound B (Scheme 11). The THP is then removed by p-toluene sulfonic acid (PTSA) in a DCM:MeOH mixture. The benzyl group is cleaved by reduction with hydrogen on Pd/C.

Preparation of Building Blocks of Category C:

Method A: The preparation of a representative building block of Category C (1C, FIG. 1) is depicted in Scheme 12 below.

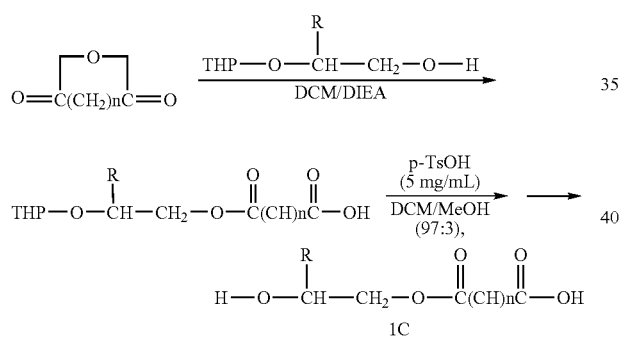

A cyclic anhydride (5 mmol, e.g., succinic anhydride, glutaric anhydride, etc.) is dissolved in dry DCM (10 ml). 2-THP-protected 2-alkyl,1,2-diol (5 mmol) and DIEA (10 mmol) are added and the reaction mixture is stirred for 16 hours. The organic phase is thereafter extracted by a saturated solution of sodium bicarbonate (2×50 ml). The aqueous phase is acidified to pH of 2-3 and extracted by DCM (3×30 ml). The combined extracts are dried over $MgSO_4$, filtered and evaporated to afford a yellow oil, which is purified on preparative HPLC.

Method B: A monoester of a dicarboxylic is coupled to a THP-protected α-hydroxyl acid in the presence of DCC and DMAP, according to the synthetic pathway depicted for Category B above, as depicted in Scheme 13 below.

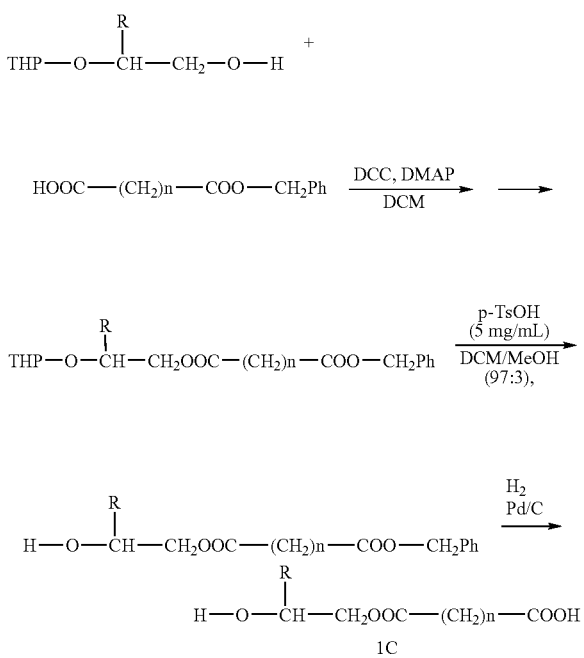

Preparation of Building Blocks of Category D:

Building blocks of category D (e.g., 1D, FIG. 1) are prepared as described above for 1C, using a protected aspartic or glutamic acid as the dicarboxylic acid, as depicted in Scheme 14 below.

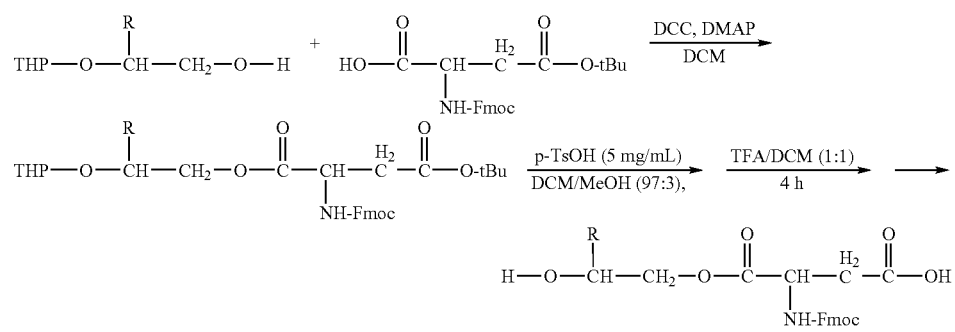

Example 11

Preparation of Heterostereoselective Complexes Containing Optically Active Polyesters An optically active polyester prepared as described herein, and a chiral macromolecule of choice (in a 1:1 mol ratio) are dissolved in an organic solvent capable of dissolving the polyester and the macromolecule (e.g., methylene chloride, N-methylpyrrolidone, or 1,1,1,3,3,3-hexafluoro-2-propanol). The solution is cast onto Petri dishes, and the solvent is slowly evaporated at room temperature for approximately 1 week, so as to avoid reaching a dried state of quasi-equilibrium. The resulting films are dried under reduced pressure for one week and are stored at room temperature for more than 1 month, so as to approach an equilibrium state prior to physical measurements.

Characterization of the obtained complexes is performed using Congo Red binding assay, according to Hatada et al. [Polym. J. 1981, 13, 811]. Ten microliters of a suspension of the complex is added to 240 microliters of 25 mM Congo red in 100 mM sodium phosphate buffer with 150 mM NaCl, pH 7.4. After a 30 minute incubation period, an ultraviolet absorbance spectrum is recorded. A red shift of 20-30 nm in the absorbance maximum of Congo red (486 nm) and hyperchromaticity are indicative of Congo red binding.

Characterization of the obtained complexes is further performed by circular dichroism spectroscopy, differential scanning calorimetry, atomic force microscopy, confocal microscopy-binding studies, SAX and molecular weight determination, as described in the Methods section hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A polymer comprising a plurality of monomer residues being linked to one another and forming a polymer backbone, at least a portion of said monomer residues comprises residues of at least one chiral monomer, wherein each of said at least one chiral monomer is independently a derivative of a chiral amino acid having the general Formula IIa or IIb:

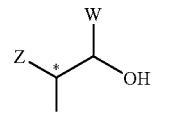

Formula IIa

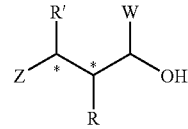

Formula IIb wherein:
each * independently denotes an R configuration or an S configuration;
each of R and R' is independently selected from the group consisting of hydrogen and a side chain of an amino acid, provided that at least one of R and R' is not hydrogen;
Z is selected from the group consisting of OH, SH and $NH_2$; and
W is selected from the group consisting of =O and RaRb, whereas each of Ra and Rb is independently hydrogen or alkyl, with the proviso that when Z is $NH_2$, W is not =O, such that said chiral monomer is not an amino acid, and with the proviso that said chiral monomer is not lactic acid,
wherein:
when the chiral monomer has Formula IIa and W is =O, said residue of said chiral monomer is linked by ester bonds to two monomer residues, said two monomer residues being independently selected from the group consisting of a residue of a monomer having Formula IIa, a residue of a monomer having formula IIb, an alkylene glycol residue, and a hydroxy carboxylic acid residue,
wherein a chirality of said chiral monomer is maintained in said monomer residues in the polymer, and further wherein an asymmetric atom in said chiral monomer forms a part of said backbone.

2. The polymer of claim 1, further comprising at least one monomer residue selected from the group consisting of a hydroxy carboxylic acid residue, a dialkylene glycol residue and a dicarboxylic acid residue.

3. The polymer of claim 1, wherein said monomer residues are linked to one another by bonds selected from the group consisting of an ester bond and an amide bond, provided that at least a portion of said bonds are ester bonds.

4. The polymer of claim 1, being a biodegradable polymer.

5. The polymer of claim 1, having a molecular weight that ranges from about 1000 Da to about 50,000 Da.

6. The polymer of claim 1, wherein said side chain of an amino acid is selected from the group consisting of —$(CH_2)_3$—NH—C($NH_2$)(=NH) (arginine side group), —$(CH_2)_4$$NH_2$ (lysine side group), —$CH_2OH$ (serine side group), —$CHOHCH_3$ (threonine side group), —$CH_2$—$C_6H_4$p-OH (tyrosine side group), —$CH_2CONH_2$ (asparagine side group), —$CH_2COOH$ (aspartic acid side group), —$(CH_2)_2$$CONH_2$ (glutamine side group), —$(CH_2)_2COOH$ (glutamic acid side group), —$CH_2SH$ (cysteine side group), —H (glycine side group), —$CH_2C$(C=CH—N=CH—NH—) (histidine side group), —$CH(CH_3)CH_2CH_3$ (isoleucine side group), —$CH_2CH(CH_3)_2$ (leucine side group), —$(CH_2)_2$$SCH_3$ (methionine side group), —$CH_2C_6H_5$ (phenylalanine side group), —CH$_2$—C(C═CH—NH-Ph-) (tryptophan side group), and —CH(CH$_3$)$_2$ (valine side group).

7. The polymer of claim 1, wherein said side chain of an amino acid is selected from the group consisting of —(CH$_2$)$_3$—NH—C(NH$_2$)(═NH) (arginine side group), —(CH$_2$)$_4$NH$_2$ (lysine side group), —CH$_2$OH (serine side group), —CHOHCH$_3$ (threonine side group), —CH$_2$—C$_6$H$_4$p-OH (tyrosine side group), —CH$_2$CONH$_2$ (asparagine side group), —(CH$_2$)$_2$CONH$_2$ (glutamine side group), —(CH$_2$)$_2$COOH (glutamic acid side group), —CH$_2$SH (cysteine side group), —H (glycine side group), —CH$_2$C(C═CH—N═CH—NH—) (histidine side group), —CH(CH$_3$)CH$_2$CH$_3$ (isoleucine side group), —CH$_2$CH(CH$_3$)$_2$ (leucine side group), —(CH$_2$)$_2$SCH$_3$ (methionine side group), —CH$_2$C$_6$H$_5$ (phenylalanine side group), —CH$_2$—C(C═CH—NH-Ph-) (tryptophan side group), and —CH(CH$_3$)$_2$ (valine side group).

8. The polymer of claim 1, further comprising residues of a dicarboxylic acid, wherein:
when W is RaRb and Z is OH and/or SH, said residue of said chiral monomer is linked by ester bonds to two dicarboxylic acid residues, and
when W is RaRb and Z is NH$_2$, said residue of said chiral monomer is linked by an ester bond to one dicarboxylic acid residue and by an amide bond to another dicarboxylic acid residue.

9. A process of preparing the polymer of claim 1, the process comprising polymerizing said at least one chiral monomer to thereby form said polymer.

10. The process of claim 9, wherein said polymerizing comprises condensing at least two of said chiral monomers.

11. The process of claim 9, further comprising, prior to said polymerizing, cyclizing said at least one chiral monomer to thereby provide a cyclic compound which comprises at least one residue of said at least one chiral monomer.

12. The process of claim 11, wherein said polymerizing comprises a ring opening polymerization.

13. The process of claim 11, wherein said cyclizing is effected in the presence of ketone and said cyclic compound further comprises a residue of said ketone.

14. The process of claim 9, wherein said polymerizing comprises an enzymatically-catalyzed polymerization.

15. A conjugate comprising the polymer of claim 1 having attached thereto an active agent.

16. The conjugate of claim 15, wherein said active agent is selected from the group consisting of a therapeutically active agent, a labeling agent, a cross-linking agent and an additional polymer.

17. The conjugate of claim 15, wherein said active agent is a therapeutically active agent.

18. The conjugate of claim 15, wherein said active agent is a chiral active agent.

19. The conjugate of claim 18, wherein said active agent forms a hetero-stereo complex with said polymer.

20. The conjugate of claim 15, wherein said polymer further comprises at least one monomer residue selected from the group consisting of a hydroxy carboxylic acid residue, a dialkylene glycol residue and a dicarboxylic acid residue.

21. A pharmaceutical composition comprising the polymer of claim 1 and a pharmaceutically acceptable carrier.

22. The pharmaceutical composition of claim 21, wherein said polymer further comprises at least one monomer residue selected from the group consisting of a hydroxy carboxylic acid residue, a dialkylene glycol residue and a dicarboxylic acid residue.

23. A method of treating a medical condition in a subject in need thereof, the method comprising administering to the subject the polymer of claim 1.

24. A pharmaceutical composition comprising the conjugate of claim 17 and a pharmaceutically acceptable carrier.

25. A hetero-stereo complex comprising the polymer of claim 1 having complexed thereto a chiral agent, said chiral agent having a stereoconfiguration suitable for forming a stereointeraction with said polymer.

26. The complex of claim 25, wherein said chiral agent is a chiral therapeutically active agent.

27. The complex of claim 25, wherein said chiral agent is selected from the group consisting of a peptide, a protein and a chiral macromolecule.

28. A method of slow-releasing an agent to an environment, the method comprising contacting a conjugate which comprises the polymer of claim 1 having the agent attached thereto, with the environment.

29. A method of slow-releasing a chiral agent to an environment, the method comprising contacting a hetero-stereo complex which comprises the polymer of claim 1 having complexed thereto said chiral agent, said chiral agent having a stereoconfiguration suitable for forming a stereointeraction with said polymer, with the environment.

30. A method of delivering a therapeutically active agent to a bodily organ of a subject in need thereof, the method comprising administering to the subject a therapeutically effective amount the conjugate of claim 17.

31. A method of treating a medical condition in a subject in need thereof, the method comprising administering to the subject a therapeutically effective amount of the conjugate of claim 17, wherein said therapeutically active agent is beneficial in the treatment of the medical condition.

32. A method of treating a medical condition in a subject in need thereof, the method comprising administering to the subject a therapeutically effective amount of the complex of claim 26, wherein said therapeutically active agent is beneficial in the treatment of the medical condition.

33. A medical device comprising the polymer of claim 1.
34. A medical device comprising the conjugate of claim 15.
35. A medical device comprising the complex of claim 25.

* * * * *